United States Patent [19]
Masterson et al.

[11] Patent Number: 5,891,094
[45] Date of Patent: Apr. 6, 1999

[54] SYSTEM FOR DIRECT HEATING OF FLUID SOLUTION IN A HOLLOW BODY ORGAN AND METHODS

[75] Inventors: Steven P. Masterson, San Francisco; Robert J. Laird, Richmond, both of Calif.

[73] Assignee: Innerdyne, Inc., Sunnyvale, Calif.

[21] Appl. No.: 877,464

[22] Filed: Jun. 17, 1997

Related U.S. Application Data

[63] Continuation-in-part of Ser. No. 525,436, Sep. 7, 1995, Pat. No. 5,653,692.
[51] Int. Cl.$^6$ .......................................................... A61F 7/12
[52] U.S. Cl. ............................... 604/113; 604/49; 604/54; 606/27; 606/31; 607/113; 607/105
[58] Field of Search ..................................... 604/113, 114, 604/118, 49, 55, 246, 181, 186, 249, 22, 20, 267, 54; 606/33, 49, 27, 32, 171, 41, 42, 31; 607/113, 122, 138, 96, 105

[56] References Cited

U.S. PATENT DOCUMENTS

| | | | |
|---|---|---|---|
| 3,312,215 | 4/1967 | Silber . | |
| 3,945,375 | 3/1976 | Banko | 128/6 |
| 4,014,343 | 3/1977 | Esty | 128/303.14 |
| 4,375,220 | 3/1983 | Matvias | 128/804 |
| 4,430,076 | 2/1984 | Harris | 604/96 |
| 4,469,103 | 9/1984 | Barrett | 128/400 |
| 4,503,843 | 3/1985 | Boebel | 128/4 |
| 4,641,634 | 2/1987 | Storz | 128/4 |
| 4,664,114 | 5/1987 | Ghodsian | 128/344 |
| 4,676,258 | 6/1987 | Inokuchi et al. | 128/804 |
| 4,779,612 | 10/1988 | Kishi | 128/6 |
| 4,820,270 | 4/1989 | Hardcastle et al. | 604/96 |
| 4,836,189 | 6/1989 | Allred, III et al. | 128/6 |
| 4,885,003 | 12/1989 | Hillstead | 604/22 |
| 4,911,148 | 3/1990 | Sosnowski et al. | 128/6 |
| 4,949,718 | 8/1990 | Neuwirth et al. | 128/401 |
| 4,955,377 | 9/1990 | Lennox et al. | 128/401 |
| 4,979,948 | 12/1990 | Geddes et al. | 606/33 |
| 5,041,093 | 8/1991 | Chu | 604/104 |
| 5,045,056 | 9/1991 | Behl | 604/49 |
| 5,100,388 | 3/1992 | Behl et al. | 604/113 |

(List continued on next page.)

FOREIGN PATENT DOCUMENTS

| | | |
|---|---|---|
| 4123418A | 4/1992 | Germany . |
| 1319848-A1 | 6/1987 | U.S.S.R. . |
| WO 81/03616 | 12/1981 | WIPO . |

OTHER PUBLICATIONS

Becker, et al., "Long–Term Occlusion of the Porcine Cystic Duct by Means of Endoluminal Radio Frequency Electrocoagulation," *Radiology*, 167:63–68, 1988.

Becker, etal., "Gall Bladder Ablation Through Radio Logic Intervention: An Experimental Alternative to Cholecystectomy," *Radiology*, 171:235–240, 1989.

Fram, et al., In Vivo Radio Frequency Thermal Balloon Angioplasty of Porcine Coronary Arteries; Histologic Effects and Safety, *American Heart Journal*, 126:969–978, 1993.

Yamanashi, et al., Properties of Electromagnetic Field Focusing Probe, *Angiology—The Journal of Vascular Diseases*, Nov. 1988, pp. 953–954.

*Primary Examiner*—Corrine M. McDermott
*Assistant Examiner*—Cris L. Rodriguez
*Attorney, Agent, or Firm*—Townsend and Townsend and Crew

[57] ABSTRACT

The invention provides improved methods and devices for heating a thermally conductive fluid within an internal body organ to thermally ablate or necrose the body organ. In an exemplary embodiment, the invention provides a thermal ablation device having an elongate member with a proximal end and a distal end. A heating apparatus is provided near the distal end of the elongate member which is constructed to heat a thermally conductive fluid without substantial direct heating of the heating apparatus. A fluid circulator is provided near the heating apparatus which circulates the thermally conductive fluid past the heating apparatus.

49 Claims, 12 Drawing Sheets

U.S. PATENT DOCUMENTS

| | | | |
|---|---|---|---|
| 5,104,377 | 4/1992 | Levine | 604/101 |
| 5,105,808 | 4/1992 | Neuwirth et al. | 128/401 |
| 5,122,122 | 6/1992 | Allgood | 604/174 |
| 5,159,925 | 11/1992 | Neuwirth et al. | 128/401 |
| 5,188,602 | 2/1993 | Nichols | 604/113 |
| 5,191,883 | 3/1993 | Lennox et al. | 128/401 |
| 5,195,965 | 3/1993 | Shantha | 604/54 |
| 5,222,938 | 6/1993 | Behl | 604/49 |
| 5,242,390 | 9/1993 | Goldrath | 604/55 |
| 5,257,977 | 11/1993 | Eshel | 604/113 |
| 5,259,836 | 11/1993 | Thurmond et al. | 604/55 |
| 5,273,526 | 12/1993 | Dance et al. | 604/35 |
| 5,275,597 | 1/1994 | Higgins et al. | 606/33 |
| 5,277,201 | 1/1994 | Stern | 607/98 |
| 5,284,486 | 2/1994 | Kotula et al. | 606/159 |
| 5,368,591 | 11/1994 | Lennox et al. | 606/27 |
| 5,370,644 | 12/1994 | Langberg | 606/33 |
| 5,423,797 | 6/1995 | Adrian et al. | 606/1 |
| 5,501,694 | 3/1996 | Ressemann et al. | 606/159 |
| 5,507,795 | 4/1996 | Chiang et al. | 606/167 |
| 5,540,658 | 7/1996 | Evans et al. | 604/101 |
| 5,542,928 | 8/1996 | Evans et al. | 604/113 |
| 5,609,602 | 3/1997 | Machemer et al. | 606/171 |

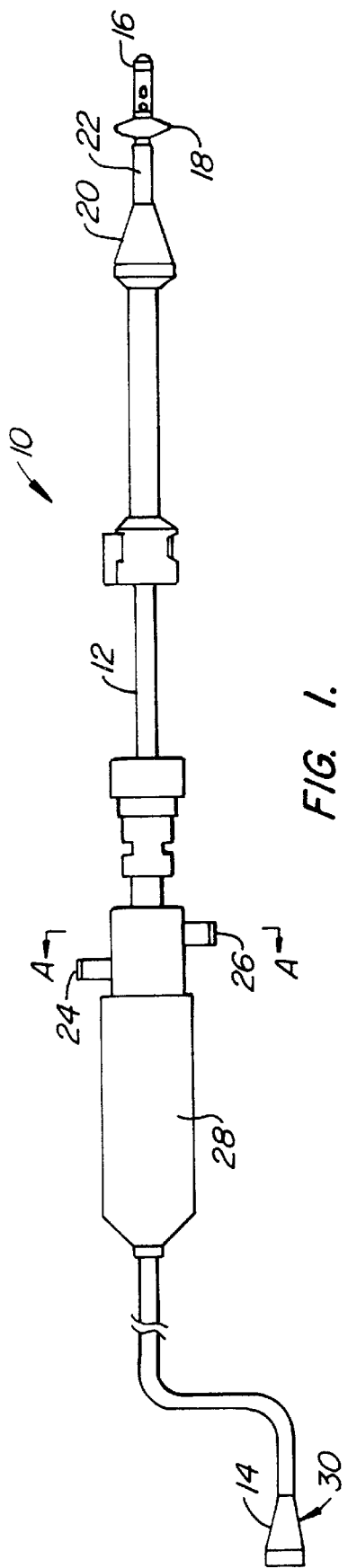
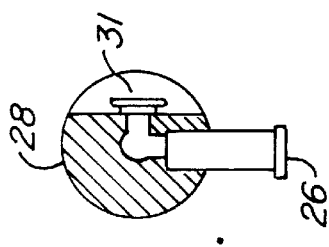
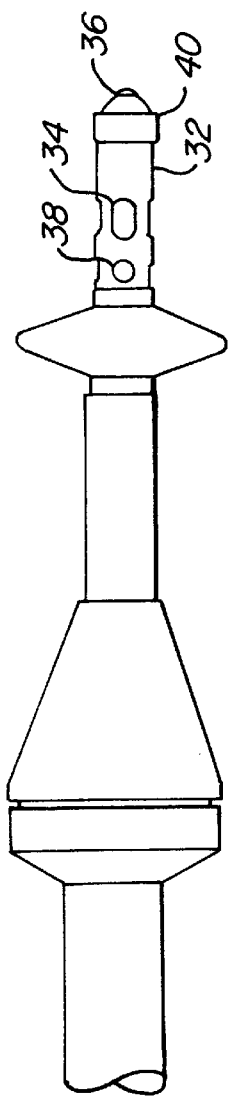
FIG. 1.
FIG. 1A.
FIG. 2.

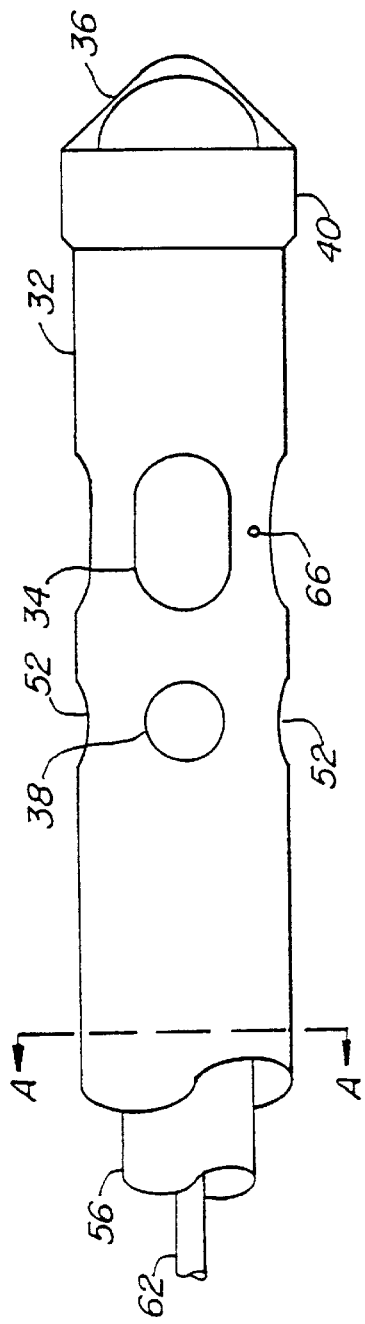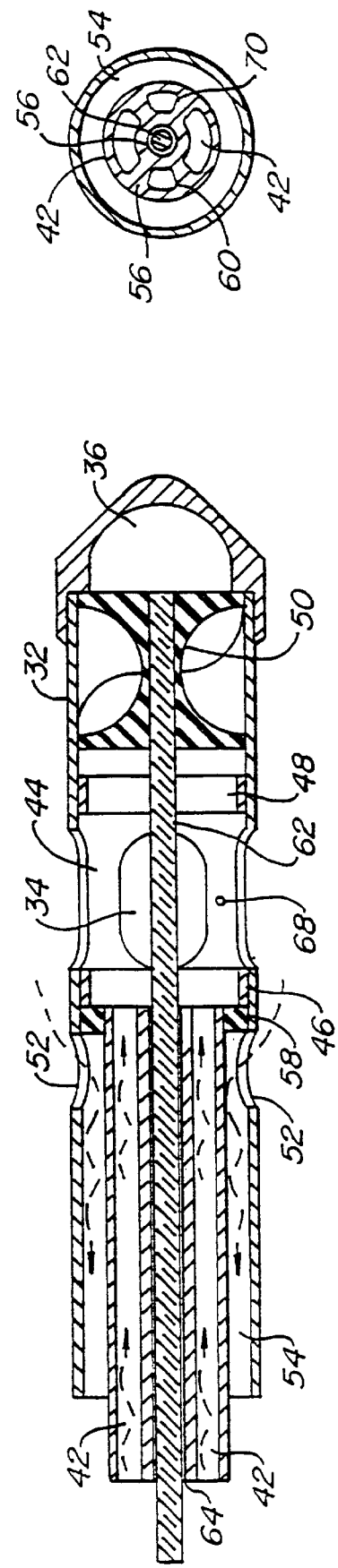

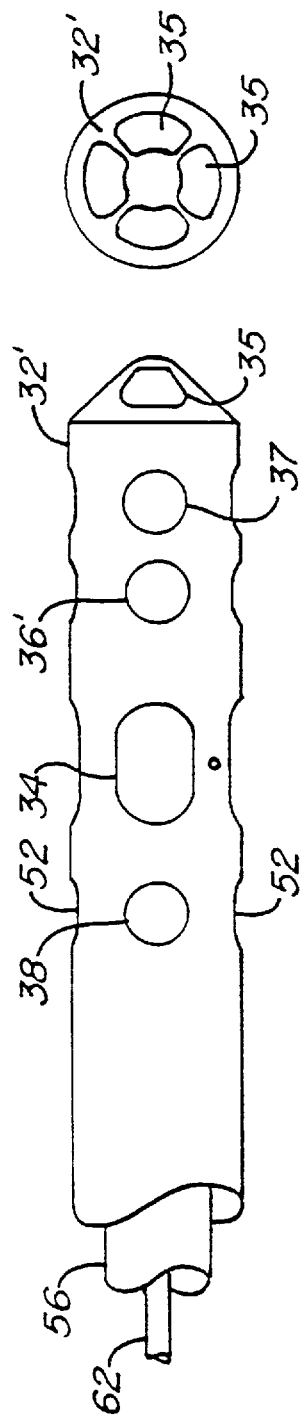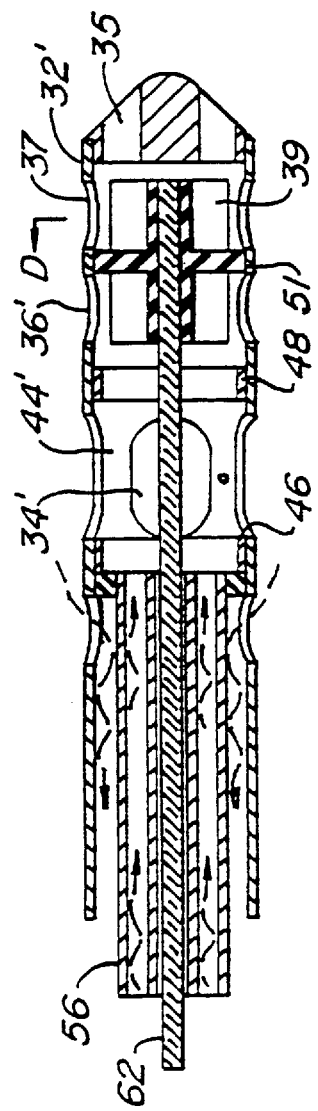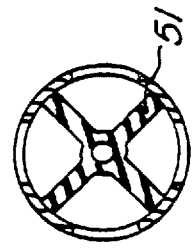

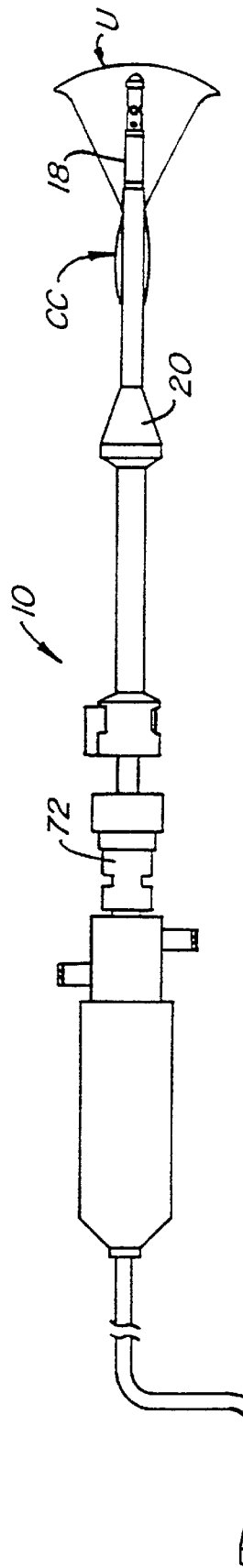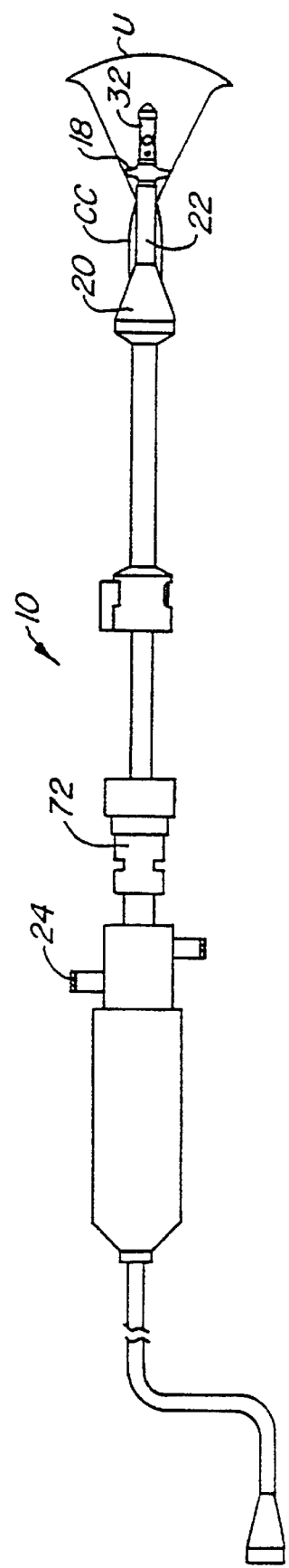

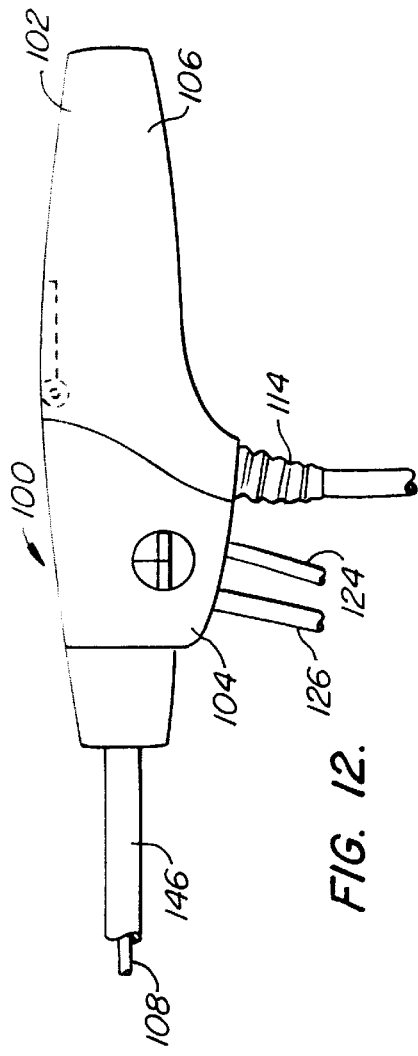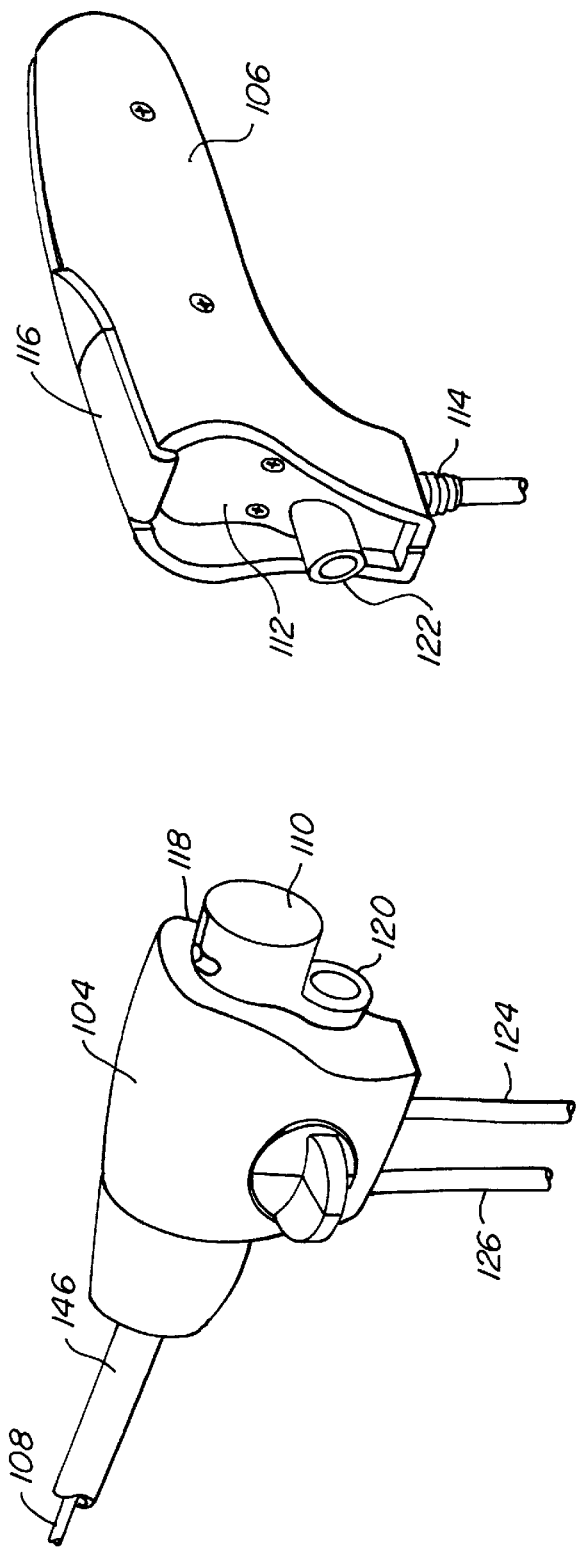
FIG. 12.
FIG. 13.

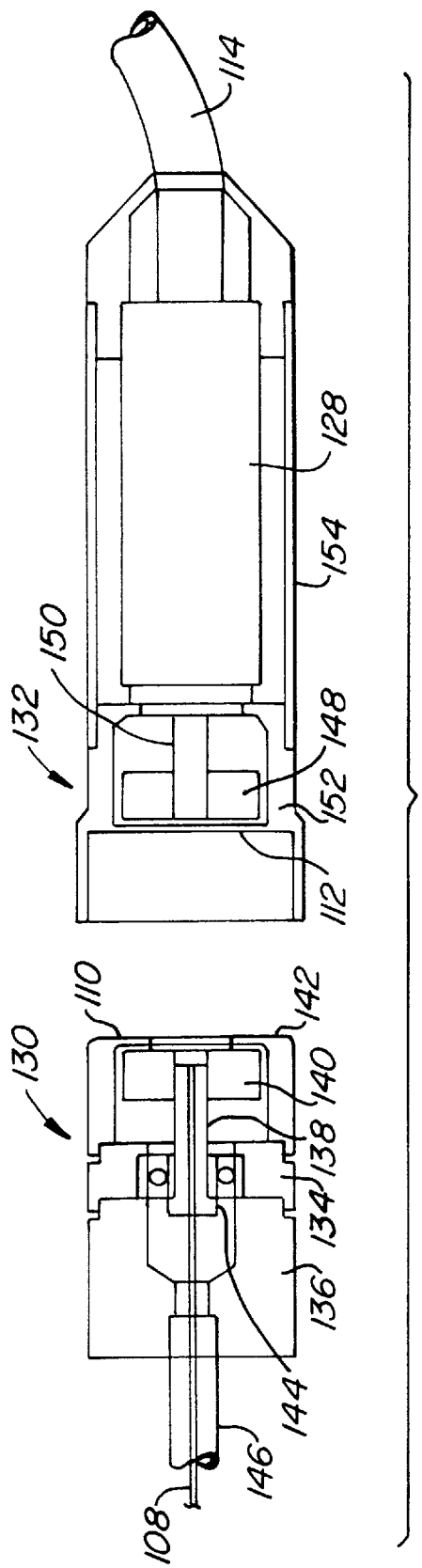
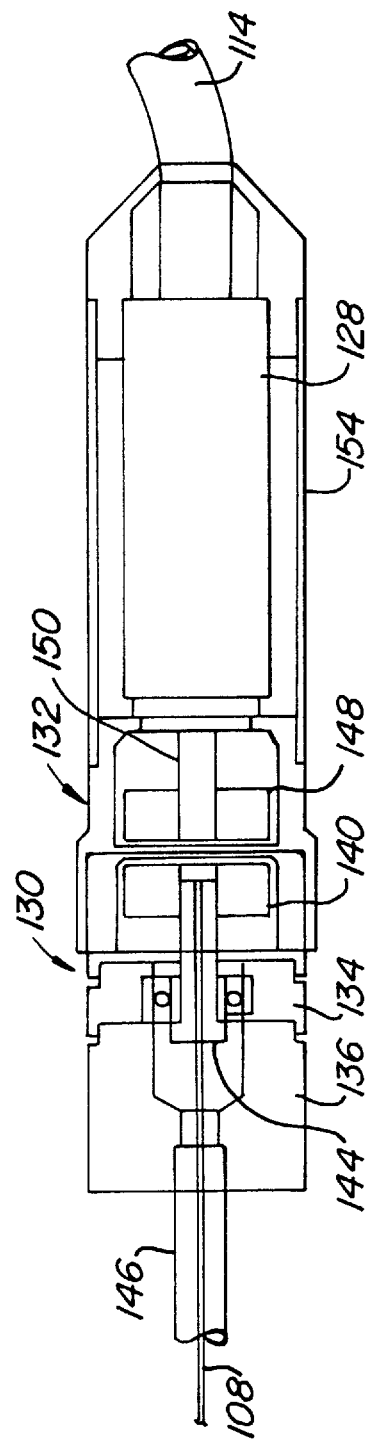
FIG. 14.
FIG. 15.

US005891094

SYSTEM FOR DIRECT HEATING OF FLUID SOLUTION IN A HOLLOW BODY ORGAN AND METHODS

CROSS REFERENCE TO RELATED APPLICATIONS

This application is a continuation in part application of U.S. patent application Ser. No. 08/525,436, filed Sept. 7, 1995, now U.S. Pat. No. 5,650,692 the complete disclosure of which is herein incorporated by reference.

BACKGROUND OF THE INVENTION

1. Field of the Invention

The present invention relates generally to the field of thermal ablation where heat is delivered to necrose or ablate a diseased body organ. More specifically, the invention provides methods and devices for thermally ablating hollow body organs, such as the uterus, by heating a thermally conductive fluid disposed within the organ.

"Minimally invasive" surgical procedures have recently been developed as alternatives to conventional "open" surgery. Of particular interest to the present invention are minimally invasive surgical procedures relating to thermal treatment of hollow body organs, and particularly to treatment of the uterus. A variety of such thermal treatment procedures have been proposed which rely on a catheter to deliver heat to the interior of hollow body organs which are filled with a thermally conductive fluid. The heated fluid is then employed to heat the mucosa sufficient to induce injury and necrosis of the organ. For example, U.S. Pat. Nos. 5,045,056; 5,100,388; 5,188,602; 5,222,938; 5,433,708; and 5,542,928, the complete disclosures which are herein incorporated by reference, describe catheters having a conductive heating element disposed on the catheter which heats a thermally conductive fluid by conventional thermal conduction to a temperature sufficient to destroy the mucosa or endothelial lining of the organ, resulting in deactivation of the organ.

Although workable, the use of such catheters having conductive heating elements at their distal ends to deliver heat within the uterus can be problematic in certain respects. For instance, heat distribution through the thermally conductive fluid can be non-uniform, thereby requiring an increase in the total amount of heat delivered to the fluid in order to assure that the temperature of all portions of the mucosa are raised above the threshold level necessary to induce injury and necrosis. However, such an increase in heat delivery may raise the temperature of some portions of the mucosa above a desired maximum temperature. Such excessive heating is undesirable in that it can in some cases result in injury to adjacent organs. As an alternative, some attempts have been made to induce an oscillatory flow between a lumen in the catheter and the organ in order to reduce the temperature gradient within the fluid. Although oscillatory mixing of the thermally conductive fluid enhances heat delivery to remote locations within the organ, mixing by inducing an oscillatory flow between the catheter lumen and the organ may be undesirable in some cases because it often creates pressure waves within the organ. Such pressure waves may be particularly problematic within the uterus because hot conductive fluid may be forced through the fallopian tubes and into the abdominal cavity, thereby potentially causing damage to adjacent. Organs oscillatory mixing is also undesirable because of potential blockage of the catheter lumen by blood clots or tissue particles that may be suspended in the fluid.

Another drawback to such conductive heating catheters is the limited capacity of their conductive heating elements to rapidly deliver necessary heat to the thermally conductive fluid. In order to deliver sufficient heat to remote portions of the organ lining, it may be necessary to raise the surface temperature of the heating element above a desired maximum temperature. However, excessive heating can result in fouling of the heating element as a result of coagulation and denaturing of blood and other proteins that may be present in the fluid, thereby reducing the heat transfer capacity of the heating element and increasing operating time.

Another problem experienced when attempting to thermally ablate a hollow body organ is the existence of air bubbles that may become trapped within the organ when introducing the thermally conductive fluid. Air bubbles trapped within the organ will tend to decrease the amount of heat transfer from the fluid to the endometrium. Further, in the case of the uterus, trapped air will tend to expand when it is heated and may cause the intrauterine fluid pressure to increase above the desired maximum, resulting in potential leakage through the fallopian tubes.

Hence, for these and other reasons, it would be desirable to provide improved methods and devices which would overcome or greatly reduce these and other problems. In particular, it would be desirable to provide methods and devices having improved heat transfer characteristics so that adequate heat may rapidly be delivered to the fluid without fouling of the heating element. The methods and devices should also provide for a uniform heating of the fluid within the organ, preferably without undesirably increasing the intraorgan pressure. In one aspect, the devices will preferably be sufficiently small to allow introduction into the uterus through the cervical canal. Further, the methods and devices should allow for the thermally conductive fluid to be introduced into the uterine cavity within a desired pressure range and so that air bubbles do not become trapped within the uterus. Finally, it would be desirable to monitor the amount of thermally conductive fluid within the hollow body organ to insure that hot fluids do not leak into surrounding areas of the body.

2. Brief Description of the Background Art

As previously described, U.S. Pat. Nos. 5,045,056; 5,100,388; 5,188,602; and 5,222,938 describe catheters having a conductive heating element that conductively heats a thermally conductive fluid within a hollow body organ.

U.S. Pat. No. 4,676,258 describes a device for radio frequency hyperthermia having a first electrode disposed in a tract or organ and a second electrode disposed on an outer circumference of a person to heat a tumor or malignancy region deep inside the person.

U.S. Pat. No. 5,368,591 describes a balloon catheter having heating electrodes disposed within the balloon.

U.S. Pat. No. 5,257,977 describes a catheter for introducing a heated fluid into the urethra.

U.S. Pat. No. 5,242,390 describes a device for introducing a heated liquid into the uterus.

U.S. Pat. No. 5,195,965 describes a catheter having a balloon for receiving a heated liquid.

U.S. Pat. No. 5,159,925 describes a catheter for laparoscopic cholecystostomy and prostate or gall bladder oblation. The catheter includes a distensible bladder at its distal end for receiving a heated fluid.

U.S. Pat. No. 4,469,103 describes a system for applying localized infrared electromagnetic energy to an effected area of a body.

U.S. Pat. No. 5,277,201 describes an endometrial ablation apparatus having an electroconductive balloon at its distal end for extending the organ and making electrical contact with the endometrial lining to be destroyed.

U.S. Pat. No. 4,430,076 describes a uterine manipulative and injector device for uterine insertion. The device includes an inflatable member at its insertable end which may be inflated to seal the lower portion of the uterus to retain fluid or gas injected into the uterine cavity.

U.S. Pat. No. 4,375,220 describes a microwave applicator for intracavity treatment of cancer.

U.S. Pat. No. 4,979,948 describes a catheter having a capacitative balloon electrode which may be expanded by an electrolyte solution to conform and make contact with the mucosal layer.

PCT Application No. WO 81/03616 describes a microwave antenna system for intracavity insertion for inducing hyperthermia by microwave irradiation.

Christoph D. Becker et al., Long Term Occlusion of the Porcine Cystic Duct by Means of Endoluminal Radio Frequency Electrocoagulation, Radiology 1988, 167:63–68 and Christoph D. Becker et al., Gall Bladder Ablation Through Radio Logic Intervention Choela and Experimental Alternative to Cholecystectomy, Radiology 1989, 171:235–240 describe gall bladder procedures using radio frequency energy.

German Pat. No. DE 4123-418-A and Soviet Union Patent No. 1319848A describe thermal urology procedures.

Daniel B. Fram et al., In Vivo Radio Frequency Thermal Balloon Angioplasty of Porcine Coronary Arteries; Histologic Effects and Safety, American Heart Journal, 1993, 126:969–978 describes a radio frequency balloon catheter having two electrodes located on the catheter shaft within a balloon lumen.

Product brochure Heads Up, Heated Balloon Catheters, Copyright 1994, describes a balloon catheter having fluid that is heated by radio frequency current flowing between electrodes disposed within the balloon.

William S. Yamanashi et al., Properties of Electromagnetic Field Focusing Probe, The Journal of Vascular Diseases, November 1988, p. 953–954 describes an electromagnetic field focusing apparatus having a radio frequency generator, a solenoid coil, and a hand-held catheter probe for producing eddy currents in biological tissues.

SUMMARY OF THE INVENTION

The invention provides methods and devices for heating a thermally (and usually electrically) conductive medium within a hollow body organ, such as the uterus, to necrose or ablate the mucosa or endothelial lining. In one exemplary embodiment, a thermal ablation device is provided having an elongate member with a proximal end and a distal end. A heating apparatus is provided near the distal end of the elongate member which is constructed to heat a thermally conductive fluid without substantial direct heating of the heating apparatus, i.e. although the heating apparatus may experience some heating during heating of the thermally conductive fluid, it is not intended that heating apparatus be employed to heat the fluid by conduction. Hence, the temperature of the heating apparatus will usually be at or only slightly above the fluid temperature while heating the fluid. The thermal ablation device is further provided with a fluid circulator near the heating apparatus to circulate the thermally conductive fluid past the heating apparatus.

In one exemplary aspect, the heating apparatus comprises a pair of spaced-apart electrodes, which are preferably ring electrodes. A radio frequency power supply is provided to supply current to the electrodes. When operated, radio frequency current passes between the electrodes and through the thermally conductive fluid (which will also be electrically conductive). As the current flows through the fluid, the fluid's natural resistance to the flow of current will generate thermal energy that will heat the fluid, with the rate of energy delivery being dictated by the square of the current multiplied by the resistance of the fluid. This energy is directly dissipated into the thermally and electrically conductive fluid. Since the electrodes themselves do not generate heat, they will generally be at or near the temperature of the fluid and thus will not become fouled by coagulation or denaturing of blood or other proteins that may be present in the fluid.

In an alternative aspect, the heating apparatus comprises a wire coil. An alternating current power supply is provided to supply alternating current to the wire coil. The varying current supplied to the coil creates a varying magnetic flux within the fluid which in turn causes eddy currents in the fluids that generates heat and increases the temperature of the fluid. Although the wire coil may experience some degree of heating as current is passed through the coil, such heating will be limited so that fouling of the wire coil will not occur. In a further alternative, microwave energy may by employed to heat the thermally conductive fluid.

In one particularly preferable aspect, the fluid circulator comprises an impeller. The impeller is provided to circulate the fluid between the electrodes or through the wire coil to provide a uniform temperature distribution within the hollow body organ. The impeller is advantageous in eliminating the need for inducing an oscillatory flow into the hollow body organ to circulate the fluid. In this way, intrauterine pressure may be maintained generally constant during circulation. Further, circulation only within the cavity eliminates potential clogging problems that may occur when introducing an oscillatory flow through a catheter lumen. Moreover, the impeller may also be fashioned to cut up clots or tissue particles within the fluid which may affect the temperature distribution of the fluid.

In another exemplary aspect, the elongate member includes a heating chamber near the distal end, with the heating apparatus and the fluid circulator being disposed within the heating chamber. Preferably, the heating chamber includes an inlet and an outlet which are disposed such that the thermally and electrically conductive fluid may be drawn through the inlet, circulated past the heating apparatus and expelled through the outlet upon the operation of the fluid circulator. Preferably, at least a portion of the elongate member is constructed of a dialectic material to isolate the electrodes from the patient.

In another aspect, an electrically insulated elongate shaft is provided and is attached at a distal end to the impeller. The shaft extends through the central lumen of the elongate member so that the impeller may be rotated by a motor located outside the patient. In a further exemplary aspect, a pair of spaced-apart occlusion members are provided about the periphery of the elongate member. The occlusion members are provided for receiving the cervical os and for forming a seal to prevent the heated fluid from escaping through the cervical canal and into the vagina. One of the occlusion members is preferably axially translatable relative to the other occlusion member. Further, one of the occlusion members is preferably radially expansible so that it may be expanded to lodge against the internal os of the cervix after being introduced into the uterus.

In still a further aspect, the thermal ablation device is provided with a temperature sensor within the chamber.

Alternatively, another temperature may be disposed on an exterior surface of the elongate member. In the event that the fluid temperature within the uterus exceeds a desired amount, the power to the heating apparatus may be discontinued. In still another aspect, the elongate member is provided with an inflow lumen and an outflow lumen. An open fluid reservoir is in communication with the inflow lumen, with the fluid reservoir holding a supply of the thermally conductive fluid. In this way, the fluid may be introduced into the hollow body organ through the inflow lumen, with gases within the hollow body being flushed through the outflow lumen. Since the fluid reservoir is open, intrauterine pressure is maintained at a generally constant pressure as dictated by the height of the fluid reservoir.

The invention provides a particularly preferable embodiment of a thermal ablation device having an elongate member with a proximal end, a distal end, and a heating chamber near the distal end. A pair of spaced-apart electrodes are disposed within the heating chamber. An impeller is also disposed within the heating chamber and is spaced-apart from the electrodes. In this manner, a thermally conductive fluid may be circulated between the electrodes upon operation of the impeller. Preferably, the electrodes will comprise ring electrodes, and a radio frequency power supply will be provided to supply current to the electrodes. The heating chamber will preferably include an inlet and an outlet which are disposed such that the thermally conductive fluid may be drawn through the inlet, circulated between the electrodes, and expelled through the outlet upon operation of the impeller.

The invention provides an exemplary method for thermally ablating a hollow body organ. According to the method, a thermally conductive fluid and a heating apparatus are introduced into the hollow body organ. The heating apparatus is then operated to heat the fluid within the hollow body organ, with the temperature of the heating apparatus generally not exceeding the temperature of the fluid while the fluid is being heated. While heating the fluid, the fluid is circulated within the hollow body organ without substantially varying the pressure within the hollow body organ. In this manner, the fluid may be quickly heated without fouling the heating apparatus. Further, generally uniform heat distribution may be obtained within the organ without substantially varying the internal pressure, which in turn may cause fluid to escape from the hollow body organ and damage adjacent organs.

In one aspect, the heating step comprises passing radio frequency current through the fluid. Alternatively, an alternating magnetic flux may be generated within the fluid to heat the fluid. In another exemplary aspect, the circulating step comprises rotating an impeller within the hollow body organ.

The invention provides a particularly preferable method for thermally ablating a hollow body organ by introducing a thermally conductive fluid into the hollow body organ. Radio frequency current is then passed through the fluid while the fluid is within the hollow body organ to heat the fluid. The fluid within the hollow body organ is continuously circulated without substantially varying the pressure within the hollow body organ. Preferably, the heating step will comprise introducing a pair of spaced-apart electrodes into the hollow body organ and passing radio frequency current between the pair of electrodes. At the same time, an impeller will preferably be rotated within the hollow body organ to circulate the fluid between the electrodes so that the fluid within the hollow body organ may be uniformly heated. Preferably, the impeller will be spun at a rate sufficient to circulate fluid and insure uniform temperature distribution, preferably being rotated in the range from about 10,000 to 30,000 revolutions per minute to circulate the fluid. In another aspect, the temperature of the fluid within the hollow body organ will preferably be monitored.

In one particularly preferable aspect, the hollow body organ will comprise the uterus. A seal will preferably be provided at the cervical os prior to circulating the fluid so that fluid will not undesirably leak through the cervical canal and into the vagina. To necrose the endothelial lining of the uterus, the fluid will preferably be heated until a substantially uniform temperature in the range from about 60° C. to 100° C. is obtained within the uterus. The intrauterine pressure will be maintained at a substantially constant pressure when circulating the fluid so that the fluid will not pass through the fallopian tubes where it may harm adjacent tissue. Preferably, the pressure will be maintained in the range from about 30 mmHg to 50 mmHg.

The hollow body organ will preferably be substantially completely filled with the fluid prior to heating and circulating the fluid. The fluid will preferably be introduced such that any gases within the hollow body organ will be flushed from the organ as the fluid is introduced into and fills the organ.

The invention provides an alternative method for thermally ablating a hollow body organ. According to the method, a thermally conductive fluid is introduced into the hollow body organ. An alternating magnetic flux is generated within the fluid to heat the fluid within the hollow body organ. The fluid is circulated within the hollow body organ without substantially varying the pressure within the hollow body organ. Preferably, the alternating magnetic flux will be generated by passing alternating current through a wire coil disposed within the hollow body organ. Such a magnetic flux causes eddy currents in the fluid which will generate heat to heat the fluid. Preferably, the fluid will be circulated through the wire coil to assist in uniformly distributing the heated fluid within the organ.

In another exemplary embodiment, the invention provides an exemplary thermal ablation system which comprises an elongate member having a proximal end, a distal end, and a heating apparatus which is operably attached to the elongate member near the distal end. A fluid circulator is also operably attached to the elongate member and includes an elongate drive shaft having a proximal end and a magnetic coupling at the proximal end. In this way, the drive shaft coupling may be magnetically coupled to a rotating magnetic coupling of a drive unit. With this arrangement, the drive unit may be employed to operate the fluid circulator, with the drive unit being both physically and electrically isolated from the fluid circulator.

In one exemplary aspect, a spacer is provided to distance the magnetic couplings when magnetically coupled together. Preferably, the drive shaft will be held within the elongate member and the spacer will comprise the proximal end of the elongate member. With this arrangement, the proximal end of the elongate member also serves to fluidically seal the elongate member from the drive unit, thereby facilitating fluid management and sterility during an operation. Further, such an arrangement provides a fluidic seal which is able to withstand relatively high rates of rotation of the drive shaft without experiencing significant wear or leakage. Since the magnetic couplings are spaced apart, the chance for current passing through the drive shaft and into the hollow body organ is greatly reduced or eliminated. Another advantage of this arrangement is that the elongate member may be constructed to be disposable, with the drive unit, which will typically house an electric motor, being reusable. A controller is also provided and includes a radio frequency power supply which may be electrically coupled to the drive unit of the heating apparatus to supply radio frequency current to heat a fluid within the hollow body organ.

In another exemplary embodiment, the invention provides a method for thermally ablating a hollow body organ by introducing a thermally conductive fluid and a heating apparatus into the hollow body organ. The heating apparatus includes a fluid circulator which is magnetically coupled to a drive unit. The drive unit is then operated to rotate the fluid circulator to circulate the heated fluid throughout the hollow body organ.

In one aspect, the fluid circulator is fluidically sealed from the drive unit. In another aspect, the fluid circulator is electrically isolated from the drive unit. With such a configuration, the heating apparatus will preferably be discarded after use, with the drive unit being reused in subsequent procedures.

In still a further embodiment, the invention provides a thermal ablation system for thermally treating a hollow body organ which is filled with the fluid. The system comprises a heating apparatus having a proximal end and a distal end. The distal end is configured to be received within the hollow body organ. A flow sensor is further provided to detect a change of volume of the fluid within the hollow body organ while the heating apparatus is in the hollow body organ. In this way, the flow sensor may be employed to detect when heated fluid is escaping from the organ into the body.

In one preferable aspect, the heating apparatus and the flow sensor are coupled to a controller which will cease operation of the heating apparatus when the flow sensor senses a change of volume that exceeds a threshold amount. In an exemplary aspect, the system further includes a fluid reservoir which may be placed in communication with the hollow body organ to fill and maintain the hollow body organ with the fluid. With this arrangement, the flow sensor preferably comprises a drip chamber and sensor for detecting droplets passing through the drip chamber. Upon detection of a predetermined number of droplets, the controller will send a signal to cease operation of the heating apparatus.

In another exemplary method of the invention, a hollow body organ is treated by inserting the distal end of the heating apparatus into the hollow body organ. The heating apparatus is then operated while monitoring the volume of fluid within the hollow body organ. In the event that a predetermined volume change of the fluid is detected, operation of the heating apparatus is ceased. Such detection preferably comprises detecting a flow of fluid from a fluid reservoir and into the hollow body organ. One exemplary way of detecting such a flow is by placing a drip chamber below the reservoir and detecting droplets of fluid falling through the drip chamber.

The invention still further provides another exemplary embodiment of a thermal ablation system for thermally treating a hollow body organ. The system comprises a heating apparatus which may be placed in a hollow body organ. A fluid reservoir is also provided along with a fluid line to fill the hollow body organ with a fluid. A first and a second one way valve are disposed in the fluid line and a plunger is placed between the first and second valves to draw fluid from the fluid reservoir and to inject a fluid into the hollow body organ. More specifically, movement of the plunger in one direction draws fluid from the reservoir and through the first valve. Movement of the plunger in another direction then moves the fluid through the second valve and into the hollow body organ.

In one exemplary aspect, the fluid line is operably attached to a lumen in the heating apparatus so that the fluid may be delivered to the hollow body organ through the heating apparatus. In another aspect, the fluid reservoir is open to the atmosphere to maintain a generally constant pressure within the hollow body organ.

The invention provides yet another exemplary method for treating the uterus. According to the method, a heating apparatus is provided which comprises an elongate body having a proximal end, a distal end, at least one heating element, and fluid circulator near the distal end. Further, the elongate body is flexible at least at the distal end. With this configuration, the distal end is introduced through the cervix until the distal end is within the uterus, with the elongate body bending within the cervix to generally center the distal end within the uterus. When properly placed within the uterus, the heating element is then operated to heat a fluid within the uterus. Preferably, the fluid circulator will also be operated during heating to circulate the fluid within the uterus. Preferably, the drive shaft used to operate the fluid circulator will also be flexible so that it may bend when inserted into the uterus.

In a further embodiment, the invention provides an exemplary thermal ablation device which comprises an elongate member having a proximal end and a distal end. A first electrode is operably attached to the elongate member near the distal end. The fluid circulator is also operably attached to the elongate member, with at least a portion of the fluid circulator being conductive so that it may serve as a second electrode. In this way, the number of components required to build the device may be greatly reduced by incorporating the second electrode into the fluid circulator.

In one aspect, the fluid circulator comprises a rotatable drive shaft and an impeller. The fluid circulator may be configured so that the drive shaft serves as the second electrode. For example, the first electrode may be constructed in the form of an annular electrode which is disposed about the shaft. Alternatively, the impeller may be constructed to be conductive and serve as the second electrode.

BRIEF DESCRIPTION OF THE DRAWINGS

FIG. 1 is a side view of an exemplary thermal ablation device according to the present invention.

FIG. 1A is a cross sectional side view of the device of FIG. 1 taken along lines A—A.

FIG. 2 is an enlarged view of a distal end of the ablation device of FIG. 1.

FIG. 3 is a more detailed view of a distal tip of the ablation device of FIG. 1.

FIG. 3A is a cross-sectional view of the distal tip of the ablation apparatus of FIG. 3 taken along lines A—A.

FIG. 4 is a cross-sectional view of the distal tip of the ablation device of FIG. 3.

FIG. 4A is an alternative embodiment of the distal tip of the ablation device of FIG. 1.

FIG. 4B is a front view of the distal tip of FIG. 4A.

FIG. 4C is a cross-sectional view of the distal tip of FIG. 4A.

FIG. 4D is a cross-sectional view of the distal tip of FIG. 4C taken along lines D—D.

FIGS. 5 and 6 illustrate an exemplary method for introducing the ablation device of FIG. 1 into a uterus according to the present invention.

FIG. 12 is a side view of proximal end of an alternative thermal ablation device according to the invention.

FIG. 13 illustrates the proximal end of the thermal ablation device of FIG. 12 separated into a disposal portion and a reusable portion.

FIG. 14 is a cross-sectional side view of a motor and a drive shaft that are housed within the two portions of the thermal ablation device of FIG. 13 and which may be magnetically coupled together according to the invention.

FIG. 15 illustrates the motor and drive shaft of FIG. 14 magnetically coupled together.

DETAILED DESCRIPTION OF THE SPECIFIC EMBODIMENTS

Figure 7:
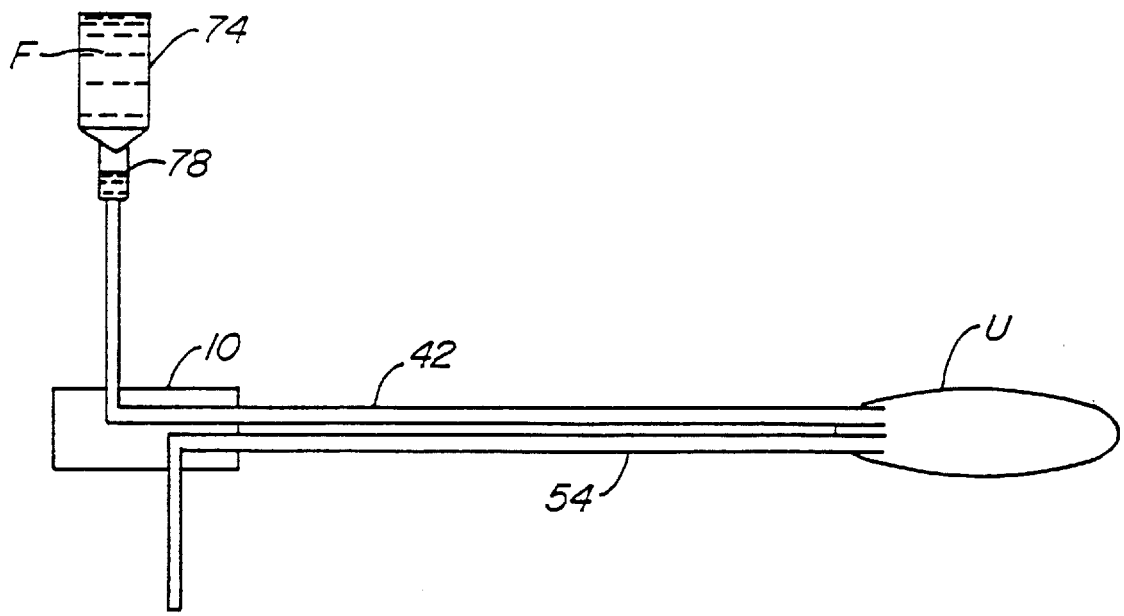
FIGS. 7–10 schematically illustrate an exemplary method for introducing a thermally conductive fluid into a hollow body organ according to the present invention.

The invention provides methods and devices for heating a thermally conductive fluid within a hollow body organ to destroy the mucosa or endothelial lining of the organ. Usually, the thermally conductive fluid will also be electrically conductive, such as when employing radio frequency current to heat the fluid. Although useful in a wide variety of hollow body organs, the present invention will find its greatest use in treating the uterus.

Thermal ablation according to the invention begins by introducing a thermally conductive fluid, such as a saline solution, into the uterus. When the uterus is filled, the invention provides for heating the fluid with a heating apparatus that is constructed to heat the fluid without substantial direct heating of the heating apparatus. Preferably, the heater will be at about the same temperature or at a slightly higher temperature, i.e., within about 3° C., of the temperature of the fluid while the fluid is being heated. In this manner, fouling of the heater will not occur since the heater will not reach a temperature which is substantially above the temperature of the fluid. Usually, the maximum temperature of the heater and the fluid will be about 95° C. or less. Heating in such a manner is further advantageous in that increased power may be supplied to the heating apparatus so that the size of the heating apparatus may be reduced. Further, since the heating apparatus of the invention will not reach excessive temperatures, the heating apparatus may be disposed closer to tissue, thereby allowing the uterus to be filled with a smaller volume of the thermally conductive fluid. With less fluid in the uterus, the fluid will more rapidly reach its desired temperature, thereby further reducing the operating time. Moreover, reduction of the volume of fluid allows for improved heat distribution within the fluid.

In one preferable aspect, such a heating apparatus will comprise two or more electrodes that are located within the uterus and are directly exposed to the fluid held within the uterus. When electric current is flowed from one electrode, through the fluid, and to the second electrode, the fluid's natural resistance to the flow of electric current will generate thermal energy that will heat the fluid. The rate of energy delivery (P) is related to the current (I) and the resistance of the fluid (R) according to the equation: $P=I^2R$.

Alternatively, the present invention may produce such heating by providing an alternating magnetic flux within the fluid which will cause eddy currents in the fluid that generate heat. Such a magnetic flux will usually be created by introducing a wire coil into the uterus and passing high frequency alternating current through the coil. Preferably, the frequency of the current will be in the range from about 100 kHz to 300 kHz. Although the coil will experience some heating when the current is passed therethrough, the fluid will be heated substantially entirely by the resulting eddy currents rather than the temperature of the coil. When using a magnetic flux to heat the thermally conductive fluid, the fluid need not be electrically conductive.

To assist in uniformly distributing the heat created by the heating apparatus of the invention, the fluid will preferably be circulated past the heating apparatus and throughout the uterus. Such circulation will preferably be accomplished without substantially varying the intrauterine fluid pressure so that heated fluid will not be forced through the fallopian tubes and damage adjacent tissue or organs. Such circulation will best be accomplished by providing an impeller or similar device which draws fluid from the uterus and directs it across or through the heater where heating occurs. In this manner, the need for an oscillatory flow through a catheter is eliminated when circulating the fluid. Use of the impeller is further advantageous in that it may be employed to cut up clots or tissue particles which may be in the fluid and which can affect the temperature distribution within the uterus.

The uterus will preferably be filled substantially completely with the thermally and electrically conductive fluid so that virtually no air bubbles will remain within the uterus. Such filling is preferably best accomplished by flushing the air from the uterus when introducing the fluid. Preferably, an open fluid reservoir (i.e., the fluid reservoir will be open to the atmosphere) will be provided to introduce the fluid into the uterus. The open reservoir is advantageous in damping pressure variations that may occur within the uterus. Further, the open reservoir may be employed to control the amount of fluid pressure within the uterus by adjusting the head of the reservoir. Preferably, the intrauterine fluid pressure will remain constant and in the range from about 30 mmHg to 50 mmHg.

Referring now to FIG. 1, an exemplary embodiment of a thermal ablation device 10 will be described. The thermal ablation device 10 includes an elongate body 12 having a proximal end 14 and a distal end 16. The elongate body 12 may be constructed of a rigid material or a semiflexible material. Disposed near the distal end 16 is a radially expansible internal os seal 18. Axially spaced-apart from the internal os seal 18 is an external os seal 20. Between the internal os seal 18 and the external os seal 20 is a reduced diameter neck 22 for receiving the cervix. Construction of the internal os seal 18, the external os seal 20, and the neck 22 are described in U.S. Pat. No. 5,540,658, the disclosure of which is herein incorporated by reference. Operation of the seals 18 and 20 will be described in greater detail hereinafter with reference to FIGS. 5 and 6.

Disposed in the elongate body 12 is a fluid inflow port 24 and a fluid outflow port 26 through which fluids may be introduced and withdrawn, respectively, to and from the uterus. The device 10 further includes a handle 28 which may optionally include an internal motor which is employed to circulate the fluid as described in greater detail hereinafter. At the proximal end 14 is a power supply connector 30 for connecting the device 10 to a radio frequency power supply as will be described in greater detail hereinafter.

As illustrated in FIG. 1A, device 10 includes a pressure sensor 31 that is disposed to monitor the intrauterine pressure when device 10 is within a patient. Sensor 31 preferably comprises a transducer which is electrically connected to a controller (not shown) so that the intrauterine pressure may be externally monitored and controlled. Sensor 31 is preferably disposed just upstream of outflow port 26 to ensure a correct pressure reading within the uterus.

Referring to FIG. 2, the distal end 16 of the device 10 will be described in greater detail. Distal to the internal os seal 18 is a distal tip 32 of the elongate body 12. The distal tip 32 may be constructed to be rigid or may alternatively be deflectable. Alternatively, the distal tip 32 may be angled relative to the elongate body 12. The distal tip 32 includes mixing inlets 34 and mixing outlets 36. As will be described in greater detail hereinafter, fluid within the uterus is drawn through mixing inlets 34, is heated within the device 10, and is then expelled back into the uterus through mixing outlets 36. A vent inlet 38 is provided and is in communication with the fluid outflow port 26 and serves to dampen pressure variations occurring within the uterus. The distal tip 32 is further provided with a blunt portion 40 to prevent tissue trauma when inserting the device 10 into the uterus.

Referring to FIGS. 3, 3A and 4, construction of the distal tip 32 will be described in greater detail. When fluid is introduced into the fluid inflow port 24, it passes through a pair of fluid inflow lumens 42 as illustrated by the dashed arrows. The incoming fluid exits the inflow lumens 42 and enters a heating chamber 44. Held within the heating chamber are a pair of spaced-apart ring electrodes 46, 48. Distal to the electrode 48 is an impeller 50. As fluid enters the heating chamber 44 from the inflow lumens 42, it passes through the electrode 46 and exists the chamber 44 through the mixing inlets 34 and mixing outlets 36. As fluid fills the uterus, gasses are removed from the uterus through exit ports 52 and into an annular fluid outflow lumen 54 where it may be withdrawn through the outflow port 26.

A multilumen tube 56 extends through the elongate body 12 and includes the fluid inflow lumens 42. A vent ring 58 is provided to isolate the fluid inflow lumens 42 from the fluid outflow lumen 54. The multilumen tube 56 further includes an electrode wire lumen 60 which serves as a conduit for electrode wires (not shown) connected to the electrodes 46, 48 and extending to the power supply connector 30.

To supply radio frequency current to the electrodes 46, 48, the power supply connector 30 is plugged into a radio frequency power supply. Preferably, radio frequency current will be supplied at a frequency in that range from 200 kHz to 300 kHz. When radio frequency power is supplied to the electrodes 46, 48, current passes through the fluid within the heating chamber 44 to heat the fluid between the electrodes. The tubing of the elongate body 12 at the distal tip 32 is preferably constructed of a dialectic material so that the electrodes 46, 48 are electrically isolated from the patient. This protects the patient from unintended contact with the electrodes which may result in electric burns and fouling of the electrodes. The electrodes 46, 48 will preferably be constructed to maximize the surface area of the electrodes and the gap between the electrodes. The size of the electrodes 46, 48 and the distance therebetween will preferably be made as large as possible without exceeding size constraints for the distal tip 32. Usually, the distal tip 32 will have an outer diameter in the range from about 3 mm to 8 mm and a length in the range from about 10 mm to 30 mm. Maximizing the surface area and the gap increases the volume of fluid being heated by the electrodes 46, 48. In this way, more fluid may be heated more rapidly, and without fouling of the electrodes 46, 48.

Although described with a pair of spaced apart electrodes 46 and 48, it will be appreciated that other arrangements of electrode designs may be provided. For example, to simplify the design and eliminate components, it may be desirable to construct either the impeller or drive shaft as one of the electrodes. In this way, a conductive impeller that is driven by an insulated shaft could be configured to be the distal electrode, thereby eliminating one of the ring electrodes and its supply wire. Similarly, one of the ring electrodes could be elongated into a cylinder and the drive shaft itself could be the second electrode. Such a configuration may also be advantageous in that it may shorten the distal tip of the device.

As previously described, fluid is circulated through the heating chamber 44 by the impeller 50. The impeller 50 pulls fluid into the heating chamber 44 through the mixing inlets 34 where it passes between the electrodes 46, 48 for heating. The heated fluid then flows out of the device 10 through the mixing outlets 36 and circulates within the uterine cavity. The impeller will be fashioned so that it will efficiently pull fluid through the inlets 34 and expel the fluid from the outlets 36 without causing pressure waves within the uterus. Preferably, the impeller will be constructed of a 180° section of a coarse thread pitch screw. A drive shaft 62 is connected to the impeller 50 and extends through a drive shaft lumen 64 of the multilumen tube 56. The drive shaft 62 will preferably be constructed of a stainless steel rod. Alternatively, the drive shaft 62 may be constructed of a wound stainless steel or a flexible plastic. Constructing drive shaft 62 to be flexible allows thermal ablation device 10 to accommodate anatomical variations which will exist from patient to patient. Further, by providing a flexible drive shaft and a flexible elongate body, the distal end of thermal ablation device 10 will tend to center itself within the cavity of the uterus when inserted. To facilitate flexible construction of thermal ablation device, the cervical seals may also be constructed to be somewhat flexible.

A proximal end of the shaft 62 is connected to a DC electric motor, which preferably spins the impeller in the range from about 10,000 to 30,000 rpm, and more preferably, at about 25,000 rpm. As previously described, the DC electric motor may be included within the handle 28 or may be separate from the device 10. The drive shaft 62 is preferably electrically insulated, e.g. with teflon, to prevent current from traveling through the shaft which could reduce power input to the thermally conductive fluid and present a shock hazard. The impeller 50 is included within the elongate body 12 to prevent it from causing tissue trauma.

The impeller 50 will preferably be operated without substantially raising the intrauterine pressure. Preferably, the impeller 50 will be configured to circulate the fluid through the heating chamber 44 at a rate sufficient to ensure that a narrow temperature differential is maintained between the fluid within the heating chamber 44 and the fluid within the uterus. Circulation of the fluid in this manner also allows more energy to be input to the electrodes without overheating the fluid between them.

The size and number of the mixing inlets 34 and mixing outlets 36 will be configured to reduce the potential of tissue or blood clots becoming clogged therein. In the event that tissue or blood clots enter into the heating chamber 44, the impeller 50 will chop the tissue or clots into small morsels to further increase heat transfer capacity of the fluid.

The device 10 is further provided with at least one temperature sensor 66 located on the outside surface of the distal tip. The temperature sensor 66 may comprise a thermocouple, a thermistor, or the like. The temperature sensor 66 is located near the mixing inlets 34 so that the temperature of the fluid entering the inlets 34 may be detected. With information provided by the temperature sensor 66, power to the electrodes 46, 48 may be controlled to in turn control the intrauterine fluid temperature. Preferably, the fluid will be heated until reaching a temperature in the range from about 60° C. to 100° C.

As best shown in FIG. 4, an internal temperature sensor 68 is provided within the heating chamber 44 to monitor the temperature within the heating chamber 44. In the event that fluid is unable to circulate through the heating chamber 44, the fluid between the electrodes 46, 48 can super heat and exceed a desired maximum fluid temperature, usually at or exceeding about 100° C. If such an event occurs, the power to the electrodes 46, 48 may be shut off. Wiring for the sensors 66 and 68 extends through a lumen 70 in the multilumen tube 56 as best shown in FIG. 3A.

An alternative embodiment of a distal tip 32' is illustrated in FIGS. 4A–4D. The distal tip 32' is essentially identical to the distal tip 32 of FIGS. 3–4 except that the distal tip 32' houses a double impeller 51 and has an additional mixing inlets and outlets. The double impeller 51 is provided to increase fluid circulation within the uterine cavity and thus improve heat distribution. The distal tip 32' includes mixing inlets 34' which cooperate with mixing outlets 36' to circulate fluid through the mixing chamber 44' and past the electrodes 46, 48 in a manner similar to that previously described with the distal tip 32 of FIGS. 3–4. The distal tip 32' further includes mixing inlets 35 which cooperate with mixing outlets 37 to circulate fluid through a secondary chamber 39. The impeller 51 pulls fluid through the mixing inlets 35 and pushes the fluid out the mixing outlets 37. This essentially doubles fluid circulation within the uterine cavity and improves heat distribution. Preferably, the impeller will be constructed of two centrifugal impellers positioned back to back.

Referring to FIGS. 5 and 6, introduction of the thermal ablation device 10 into the uterus U through the cervical canal CC will be described. As shown in FIG. 5, the device 10 is transcervically introduced into the uterus U until the internal os seal 18 passes entirely through the cervical canal CC and into the uterus. An actuator 72 is then distally advanced to radially expand the internal os seal 18 as illustrated in FIG. 6. The device 10 is then proximally withdrawn to seat the internal os seal 18 against the internal os of the cervix. The external os seal 20 is then advanced to seat the seal 20 against the external os the he cervix, with the neck 22 lying within the cervical canal CC. The external os seal 20 is then locked to hold the seals 18, 20 in place. Once a suitable seal is formed, fluid is introduced into the uterus U through the inflow ports 24 as previously described. When the uterus U is filled with the fluid, heating may then proceed by energizing the electrodes as previously described. In this way, heating occurs within the uterus U so that heated fluid is not exposed to the cervical canal CC or to the vagina.

Figure 8:
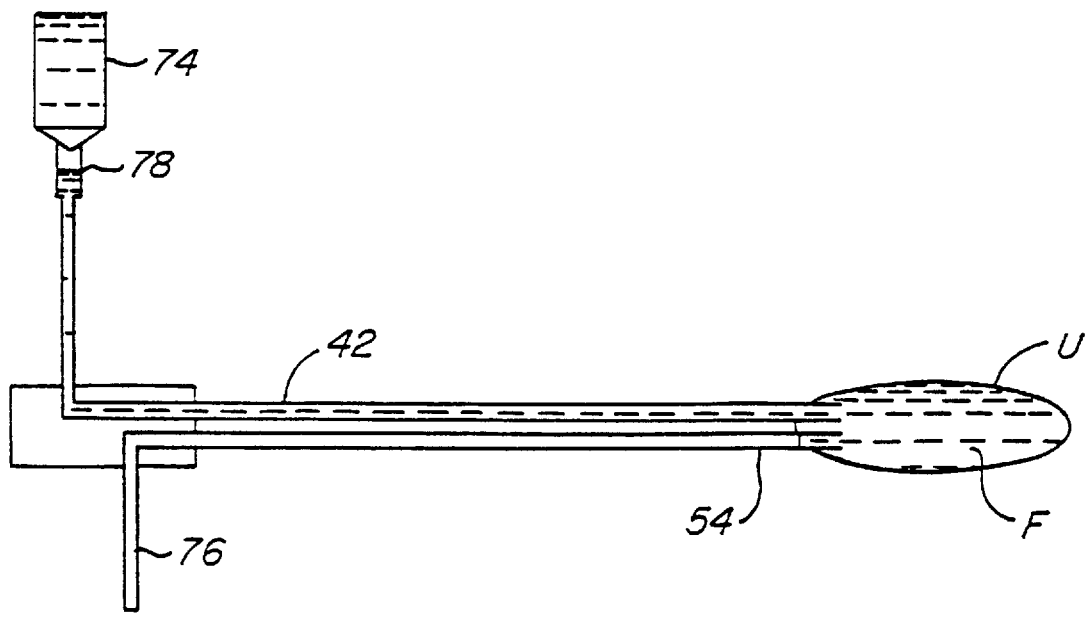
Figure 9:
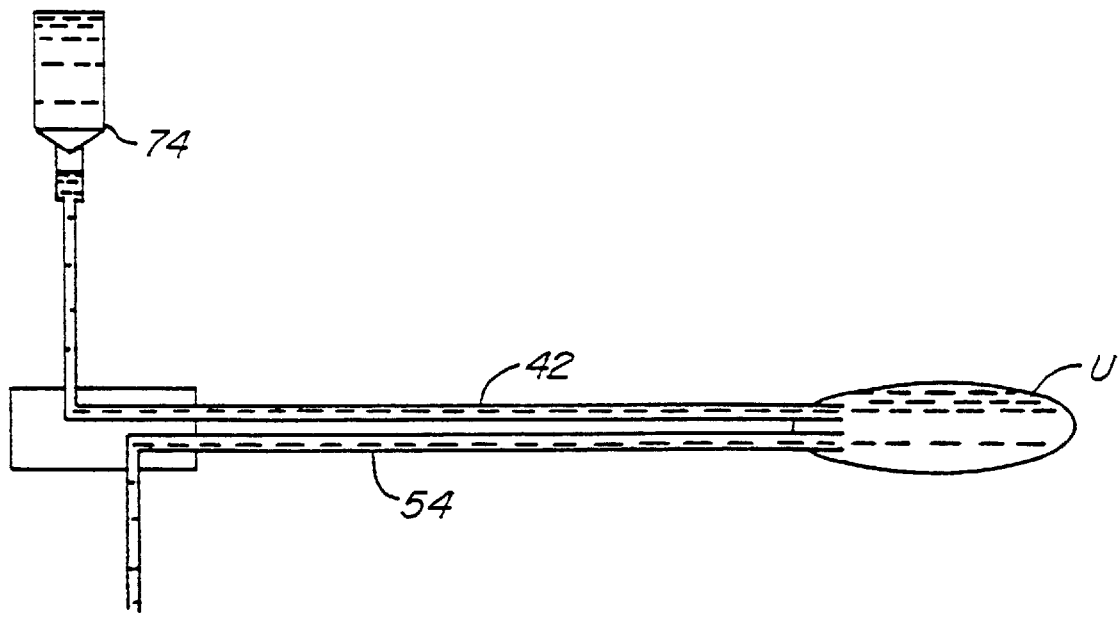
Figure 10:
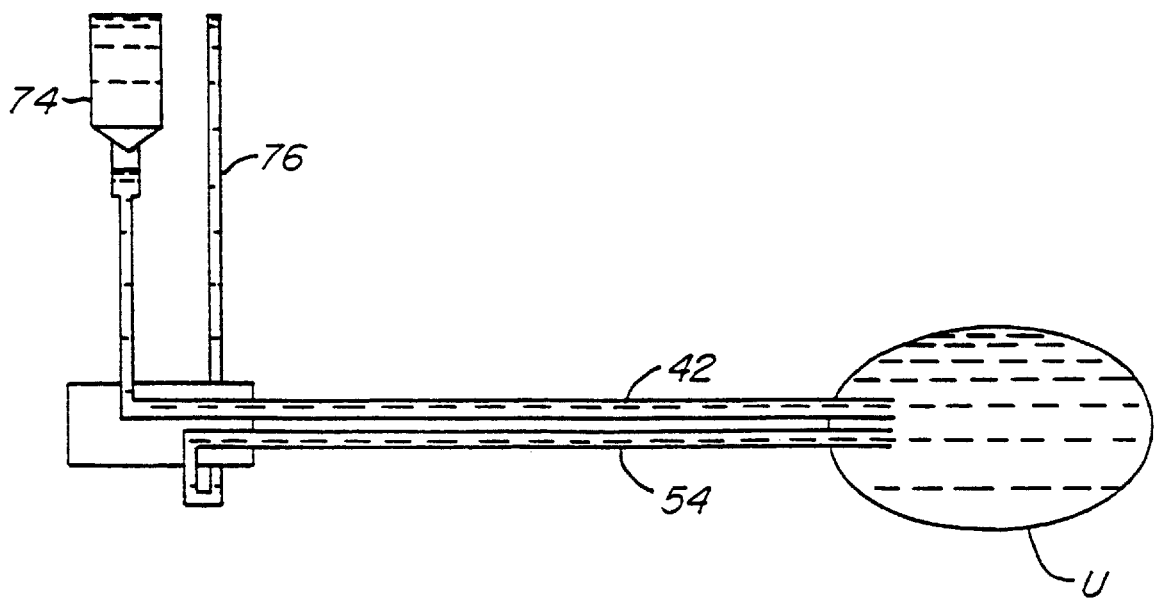

Referring to FIGS. 7–10, an exemplary method for filling the uterine cavity U with a thermally conductive fluid will be described. For convenience of discussion, reference numerals used to describe the thermal ablation device 10 will be used for like elements in the schematics of FIGS. 7–10. Operation of the thermal ablation device 10 to fill and maintain fluid within the uterus U will preferably proceed in a manner substantially identical to the procedure set forth schematically in FIG. 7–10. To fill the uterus U with fluid, an open fluid reservoir 74 having the fluid F is connected to the fluid inflow lumen 42 as shown in FIG. 7. Preferably, the fluid reservoir 74 will be elevated above the uterus U at a height sufficient to produce the desired intrauterine pressure. Preferably, the open fluid reservoir 74 will be a saline bag that is elevated from about 16 inches to about 27 inches above the uterus to produce a pressure in the range from about 30 mmHg to 50 mmHg within the uterus U. As fluid flows through the inflow lumen 42, it enters the uterus U as illustrated in FIG. 8. Air within the uterus U is expelled through the outflow lumen 54. Optionally, the flow of fluid through the inflow lumen 42 may be restricted relative to the outflow lumen 54 to improve air removal from the uterus U. Further, a tube 76 may be attached to the outflow lumen 54 and hung below the uterus so that as fluid flows through the tube 76 a vacuum will be generated in the uterine cavity because of the restricted flow through the inflow lumen 42. The vacuum will tend to collapse the uterine cavity and suck the air from the uterus U. After the air is removed from the uterus U, the outflow lumen 54 will be primed and may be closed to allow the fluid F in the reservoir 74 to pressurize and distend the uterus U. If the intrauterine pressure unexpectedly increases, the excess pressure will naturally vent through the inflow lumen 42 and into the fluid reservoir 74. Further, as previously described, the vent inlet 38 on the device 10 is provided to allow undesirable pressure variations to be vented back through the fluid outflow port 26. In the unlikely event that fluid leaks from the uterine cavity, the fluid reservoir 74 may be employed to replenish the lost fluid to maintain the desired intrauterine pressure. Optionally, the reservoir 74 may be provided with a drip chamber 78 so that flow from the reservoir 74 can be monitored and controlled. As illustrated in FIG. 10, once the entire system is primed with the fluid F, the outflow tube 76 may be raised to the height of the fluid reservoir 74 to maintain the desired intrauterine pressure. Alternatively, outflow tube 76 may simply be closed.

Figure 11:
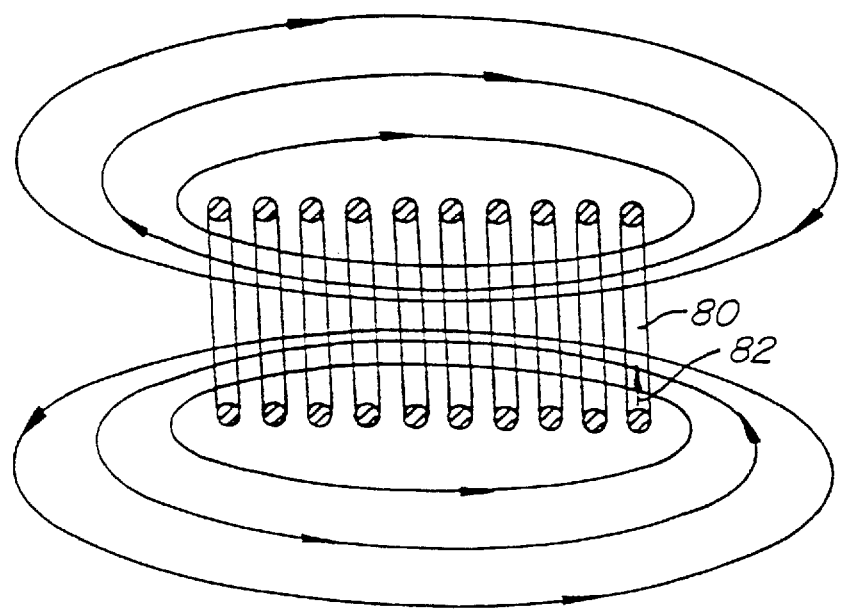
FIG. 11 is a cross-sectional view of a coil showing the distribution of magnetic flux when current is passed through the coil.

Referring to FIG. 11, a wire coil 80 is shown in cross-sectional view. The wire coil 80 may be employed as a substitute for the electrodes 46 and 48 of the thermal ablation device 10. To heat fluid using the wire coil 80, high frequency alternating current at a frequency in the range from 100 kHz to 300 kHz is directed through the wire coil in the direction indicated by the arrow 82. When electrical current is passed through the wire coil 80 in this manner, a magnetic flux is created. The magnetic flux distribution is illustrated with elliptical circles in FIG. 11, with the density of the flux being greatest inside the coil 80. The varying magnetic flux within the fluid in turn causes eddy currents in the fluid that generate heat. In this manner, fluid within the heating chamber 44 may be heated by the wire coil 80.

Referring now to FIG. 12, an alternative embodiment of a thermal ablation device 100 will be described. Shown in FIG. 12 is a proximal end 102 of thermal ablation device 100, it being appreciated that the distal end may be constructed to be essentially identical to the distal end of thermal ablation device 10, as previously described. Proximal end 102 comprises a disposable portion 104 and a reusable portion 106 which functions as a drive unit. Reusable portion 106 will preferably include a motor (not shown)

which is employed to rotate a drive shaft 108 on disposable portion 104. In turn, drive shaft 108 rotates an impeller at the distal end of thermal ablation device 100 in a manner similar to that previously described with other embodiments.

Referring also now to FIG. 13, disposal portion 104 and reusable 106 are shown separated in order to facilitate description of proximal end 102. Disposable portion 104 and reusable portion 106 each house a magnet which cooperate together to couple the motor within reusable portion 106 with drive shaft 108 in disposable portion 104. Further, disposable portion 104 includes a magnetic interface 110 which is placed adjacent to a magnetic interface 112 on reusable portion 106 when portions 104 and 106 are coupled together as illustrated in FIG. 12. In this way, when portions 104 and 106 are coupled together, the motor within reusable portion 106 is magnetically coupled to drive shaft 108 in disposable portion to allow drive shaft 108 to be rotated upon operation of the motor. An electric cable 114 is coupled to reusable portion 106 to supply electrical current to the motor. Conveniently, a mechanism is provided to attach motor to disposable portion 106. Such a mechanism may comprises, for example, a locking tab 116 is provided on reusable portion 106 and will engage a recess 118 on disposable portion 104 to securely attach portions 104 and 106 when coupled together.

Portions 104 and 106 each further include an electrical connector 120 and 122 which are electrically coupled together when portions 104 and 106 are attached to each other. Electrical connector 122 is further coupled to electric cable 114 so that radio frequency current may be supplied to the electrodes located at the distal end of thermal ablation device 100 in order to heat the thermally conductive fluid as previously described in connection with thermal ablation device 10. Hence, electric cable 114 may be provided with separate wires, some being electrically coupled to the motor to rotate the drive shaft and others being electrically coupled to electrical connector 122 to provide radio frequency current to the electrodes. Electric cable 114 will preferably be electrically coupled to a controller, having both a power supply for the motor and for the electrodes to provide the necessary power as described in greater detail hereinafter. Optionally, a separate cable could be electrically coupled directly to disposal portion 104 to provide radio frequency power to the electrodes.

Disposable portion 104 further includes a fluid inflow line 124 and a fluid outflow line 126 to allow a thermally conductive fluid to be introduced into and withdrawn from the hollow body organ in a manner similar to that previously described with thermal ablation device 10. Drive shaft 108 rotates within an elongate body 146 which also serves as a conduit for the thermally conductive fluid as described in previous embodiments.

Configuration of proximal end 102 provides a number of significant advantages, including the ability to discard disposable portion 104, and the ability to reuse reusable portion 106. Since reusable portion 106 will include an electrical motor, significant cost savings may be obtained by reusing the motor. Further, by providing magnetic interface 112, the motor may be sealed within reusable portion 106 to allow reusable portion 106 to be subjected to multiple sterilization cycles, i.e., autoclaving, ETO sterilization, soaking, and the like.

One particular advantage of terminating drive shaft 108 within disposable portion 104 is that a fluidic seal is provided between disposable portion 104 and the motor via magnetic interface 110. In this way, the need for a fluidic seal directly around the drive shaft (which can rotate at 10,000 rpm or more and wear out the seal) is eliminated. Hence, fluids can conveniently be introduced and withdrawn to and from lines 124 and 126 without a concern for having the fluids enter into reusable portion 106 to interfere with the motor. Further, by physically separating drive shaft 108 from the motor within reusable portion 106, a significant amount of electrical isolation is provided between drive shaft 108 and the electrical motor. In this way, the possibility of current passing through drive shaft 108 and into the hollow body organ is greatly reduced or eliminated. In yet another advantage, by providing disposable portion 104 as a separately sealed unit, fluids may be more safely introduced into and withdrawn from the hollow body organ without being contaminated by the electrical components within the reusable portion 106.

Referring now to FIGS. 14 and 15, construction of drive shaft 108 to magnetically interface with a motor 128 (which in turn is held within reusable portion 106 of FIG. 13) will be described. Drive shaft 108 is operably attached to a magnetic coupling assembly 130 which includes magnetic interface 110 of disposable portion 104 (see FIG. 13). Similarly, motor 128 is operably connected to a magnetic coupling 132 which includes magnetic interface 112 of reusable portion 106 (see FIG. 13). In this way, when magnetic coupling assembly 130 and 132 are coupled together, operation of motor 128 will rotate drive shaft 108.

Coupling assembly 130 comprises a bearing 134, a hub 136, a coupling 138 and a magnet 140. Magnet 140 is held within an end cap 142 which includes magnetic interface 110. Coupling assembly 130 is preferably constructed by securing bearing assembly 134 within the housing defined by disposable portion 104 (see FIG. 13). Bearing assembly 134 will preferably be securely attached to the housing so that it can accommodate any torsional or axial loads. Coupling 138 is then installed into bearing assembly 134, preferably by bonding, to accommodate for any torsional loads. Coupling 138 includes a shoulder 144 which sits against bearing assembly 134 and acts as a mechanical stop for axial loads that are generated by the magnetic attraction of magnet 140 to magnetic coupling assembly 132. Coupling 138 and bearing assembly 134 also assist to maintain axial alignment of drive shaft 108.

Bearing assembly 134 is then affixed to hub 136 and magnet 140 is affixed to coupling 138. An assembly spacer may optionally be provided between magnet 140 and bearing assembly 134 during assembly to achieve proper axial alignment. Such a spacer will then be removed after assembly. Finally, drive shaft 108 is affixed to coupling 138. To complete the assembly, end cap 142 is affixed to bearing assembly 134.

Coupling assembly 132 comprises a magnet 148 which is affixed to a drive shaft 150 of motor 128. Electric cable 114 is coupled to motor 128 to supply the necessary power to operate motor 128. Magnet 148 is held within an end cap 152 which includes magnetic interface 112. In this way, motor 128 is physically isolated from magnetic coupling assembly 132. Conveniently, motor 128 is held within a motor housing 154 which protects motor 128 during sterilization of reusable portion 106, as previously described.

When coupling assemblies 130 and 132 are coupled together, interface 110 will be adjacent interface 112 as illustrated in FIG. 15. In turn, magnets 140 and 148 will be magnetically coupled together. In this way, when motor 128 is operated to rotate drive shaft 150, a torsional force is transferred from magnet 148 to magnet 140, which in turn rotates drive shaft 108.

Figure 16:
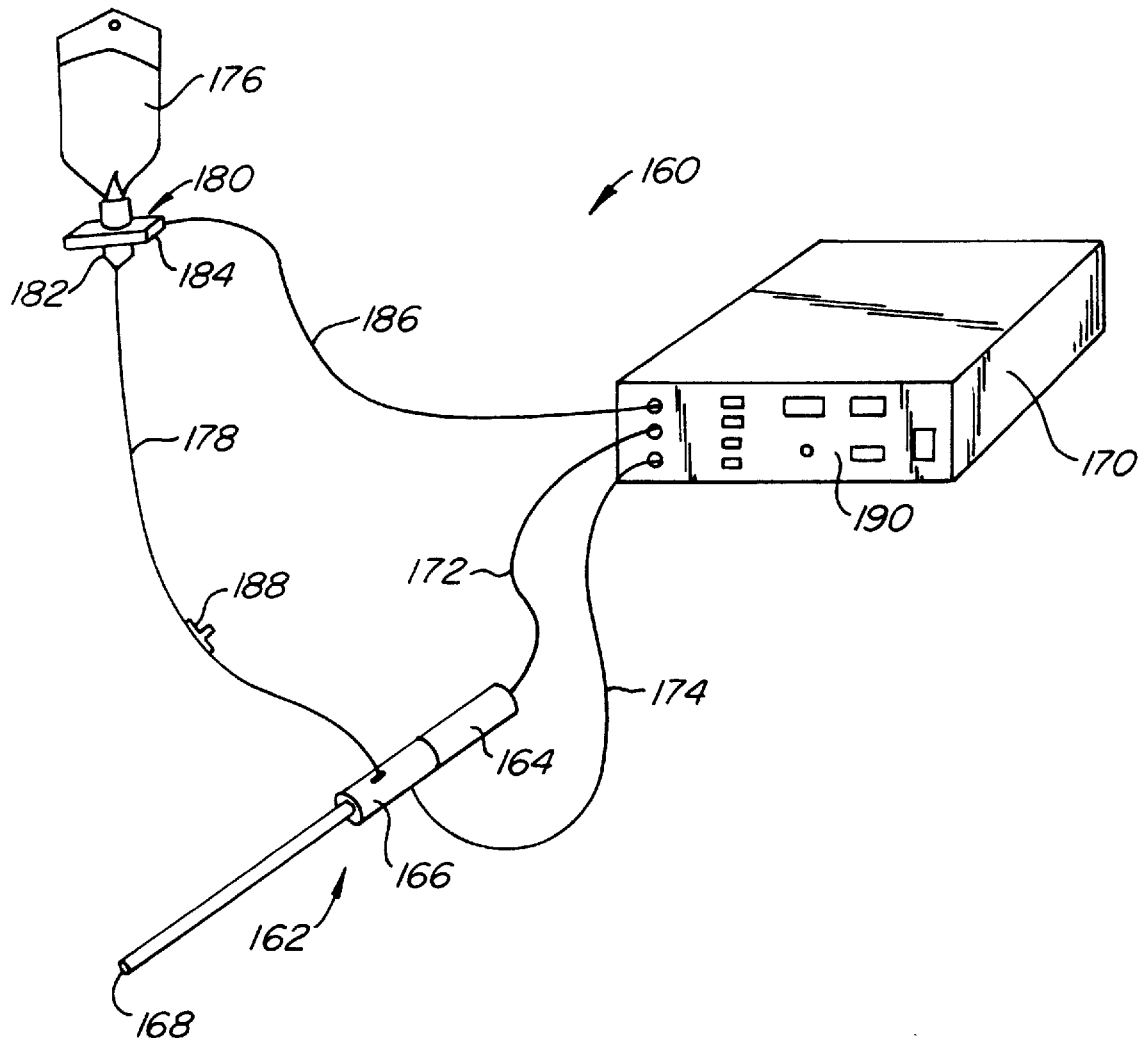
FIG. 16 illustrates an exemplary system for thermally treating a hollow body organ according to the invention.

Referring now to FIG. 16, an exemplary system 160 for thermally treating a hollow body organ will be described. System 160 comprises a thermal ablation device 162 which is constructed similar to thermal ablation device 100, as previously described. In particular, thermal ablation device comprises a reusable drive unit portion 164 and a disposable portion 166. Reusable portion 164 includes an electric motor (not shown), while disposable portion 166 includes a drive shaft (not shown) for rotating an impeller at a distal end 168 similar to thermal ablation device 10, as previously described. The motor in reusable portion 164 is electrically coupled to a power supply within a controller 170 via an electrical cable 172.

Disposable portion 166 is electrically coupled to a radio frequency power supply within controller 170 via an electrical cable 174. However, it will be appreciated that cables 172 and 174 may be combined, with an electrical interface being provided between portions 164 and 166 to allow radio frequency current to be supplied to disposable portion 166 via reusable portion 164 similar to thermal ablation device 100, as previously described. The radio frequency power supply within controller 170 supplies radio frequency current to electrodes disposed near distal end 168 to allow a thermally conductive fluid to be heated within a hollow body organ as previously described in connection with thermal ablation device 10. Electrical cable 174 further includes wiring to electrically connect controller 170 to temperature and pressure sensors which are disposed on device 162 to monitor the temperature and pressure within the hollow body organ similar to thermal ablation device 10 as previously described.

Although not shown, a fluid inflow line and a fluid outflow line will be coupled to disposable portion 166 similar to those described with thermal ablation device 100 to introduce and remove a thermally conductive to and from the hollow body organ. System 160 further includes a fluid reservoir 176 (shown in the form of a saline bag) to maintain an equilibrium amount of the thermally conductive fluid within the hollow body organ as previously described. Fluid reservoir 176 is placed in fluid communication with disposable portion 166 through a fluid line 178. System 160 further includes a flow control sensor 180 to monitor the flow of liquid from fluid reservoir 176 and into the hollow body organ. In this way, the care giver may be alerted to the possibility of a leak that is occurring within the hollow body organ. For example, heated fluids may undesirably escape through the fallopian tubes. By detecting a flow of liquid from fluid reservoir 176, the care giver may be alerted to a possible leak somewhere within system 160 or within the patient.

Flow system 180 preferably comprises a drip chamber 182 and a drip sensor 184 to sense when liquid from fluid reservoir 176 is passing through drip chamber 182 and into fluid line 178. Preferably, drip sensor 184 will comprise an infrared sensor which is used to generate an electrical signal that is sent to controller 170 via a line 186. Controller 170 may then be programmed to stop operation of thermal ablation device 162 when a threshold amount of liquid has passed through drip chamber 182.

Fluid reservoir 176 is further provided to assist in flushing the hollow body organ with liquid prior to treatment. To facilitate such a process, a flushing valve 188 is provided within fluid line 178. Operation of flushing valve 188 will be described in greater detail with reference to FIGS. 18 and 19.

Figure 17:
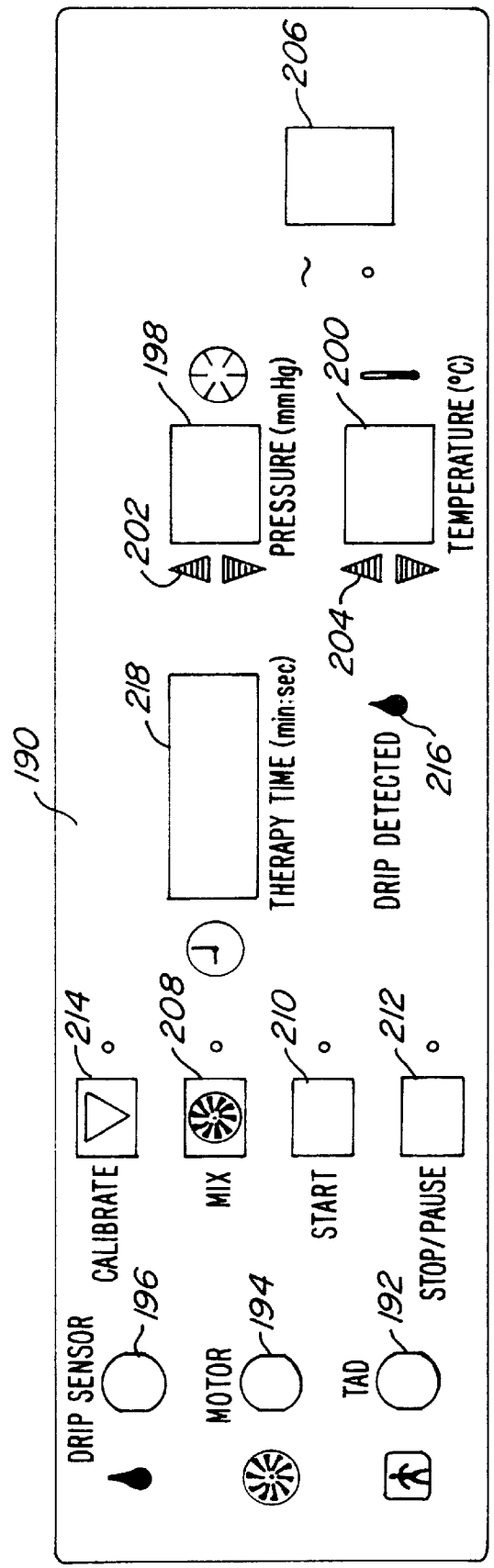
FIG. 17 is a front view of a controller of the system of FIG. 16.

Referring now to FIG. 17, a control panel 190 of controller 170 will be described. Panel 190 includes a thermal ablation device connector 192, a motor connector 194, and a drip sensor connector 196. Electrical cable 174 is electrically coupled to connector 192. In turn, connector 192 is coupled to a radio frequency power supply within controller 170 to provide radio frequency current to the heating electrodes. Connector 192 is further coupled to a temperature and a pressure monitor within controller 170 so that the temperature and pressure within a hollow body organ can be both measured and monitored. Control panel 190 further includes a pressure display 198 and a temperature display 200 to display the pressure and temperature within the hollow body organ. Conveniently, such displays may be constructed to be LED panels. Associated with pressure display 198 and temperature display 200 are touch sensitive tabs 202 and 204 which may be depressed to vary the pressure and temperature within the hollow body organ. For example, when tab 204 is depressed, controller 170 will adjust the amount of current passing between the electrodes. Conveniently, an on/off button 206 is provided to actuate controller 170.

Motor connector 194 may be electrically coupled to electrical cable 172 to provide electrical current to the motor within reusable portion 164 to operate the motor. A mix button 208 is provided on panel 190 to actuate the motor, which in turn will rotate the impeller on thermal ablation device 162. Similarly, a start button 210 is provided on panel 190 to initiate the heating process within the hollow body organ. A stop/pause button 212 is further provided to stop the flow of radio frequency current, thereby stopping the heating process. A calibration button 214 is provided on control panel 190 to calibrate the pressure transducer within thermal ablation device 162 to atmospheric pressure. In this way, more accurate pressure measurements within the hollow body organ may be obtained.

Drip sensor 196 may be electrically coupled to line 186 so that controller 170 may monitor the volume of fluid exiting fluid reservoir 176 and passing into the hollow body organ. Once a threshold volume of liquid has been sensed, controller 170 will stop the flow of current to connectors 192 and 194 to stop operation of thermal operation device 162. Further, a drip display 216 may be provided on panel 190 to give a visual indication of each drip that is detected.

Panel 190 further includes a timer 218 which may be employed to set a desired operation time. Upon expiration of timer 218, controller 170 will stop operation of thermal ablation device 162.

Controller 170 preferably further includes sensors which monitor the state of the motor, i.e., its speed, load, and the like, and will be configured to stop operation of the motor when certain threshold values are exceeded. Further, controller 170 may be provided with a variety of alarms to indicate abnormal operating conditions, such as over or under temperature, over or under pressure, fluid volumes exiting from fluid reservoir 176, failure of thermal ablation device 162, motor failure, general electrical fault, and the like. In the event that certain conditions are detected, controller 170 is configured to cease operation of device 162 to provide increased safety to the patient.

Figure 18:
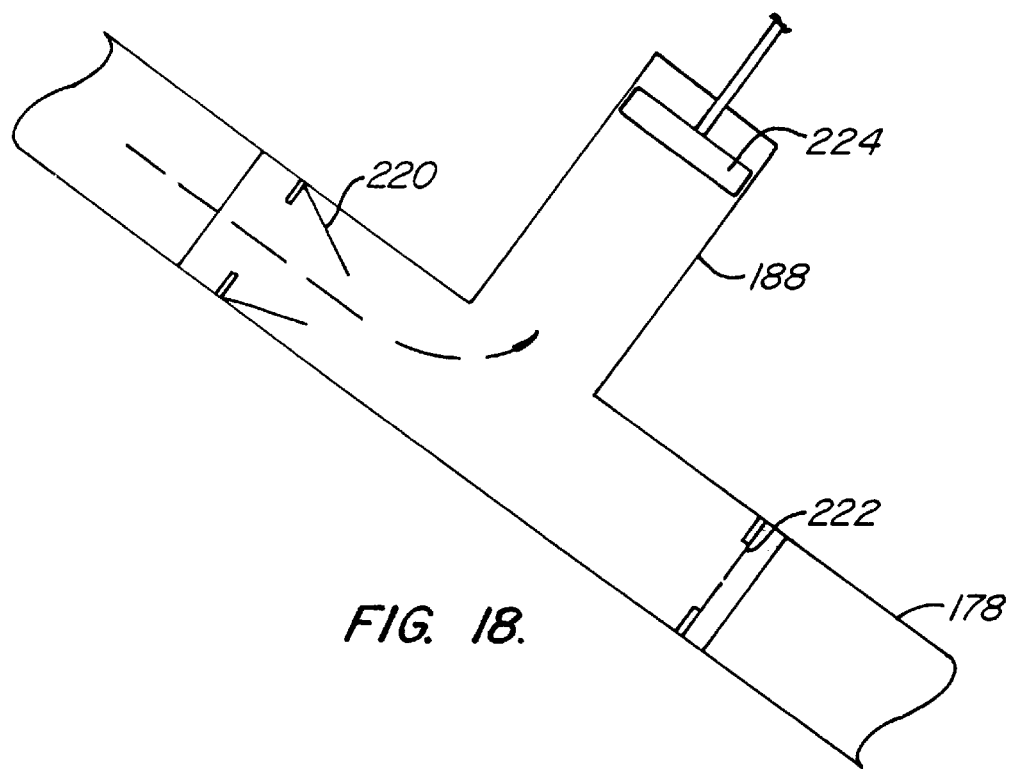
FIG. 18 is a cross-sectional side view of a flush system included within the thermal ablation system of FIG. 16.
Figure 19:
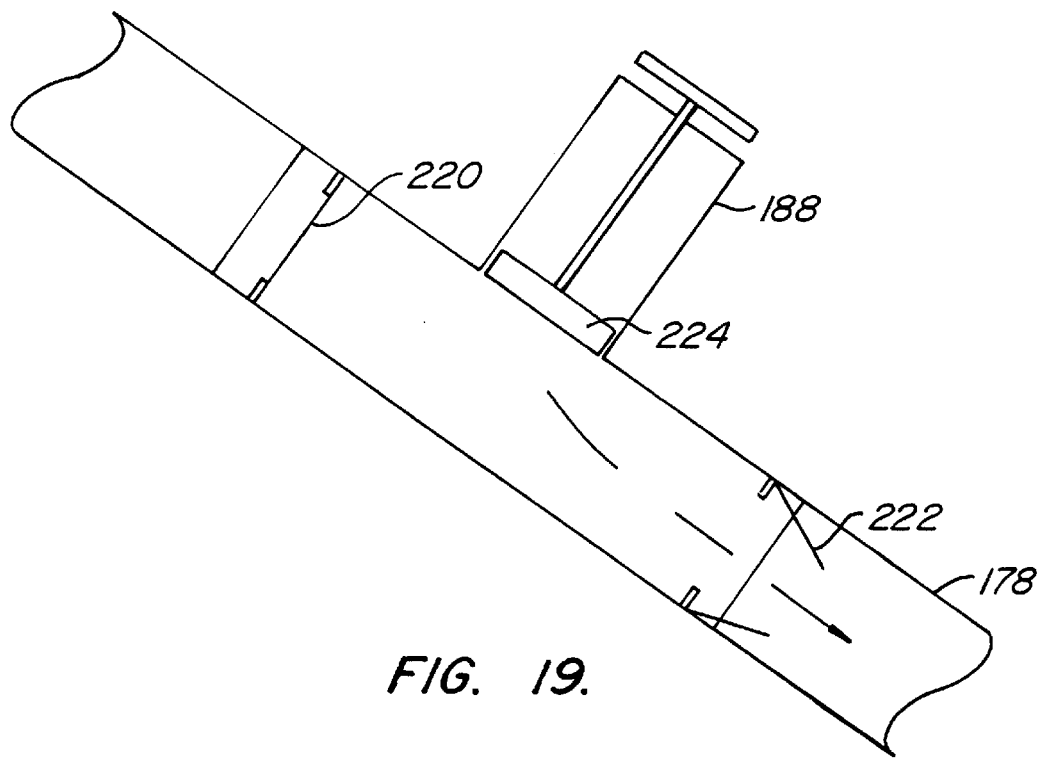
FIG. 19 illustrates the flush system of FIG. 18 with a valve closed to flush a fluid into the hollow body organ according to the invention.

Referring now to FIGS. 18 and 19, construction of flushing valve 188 (see FIG. 16) will be described in greater detail. Flushing valve 188 is provided with a pair of one-way valves 220 and 222. Valves 220 and 222 are preferably constructed to provide minimal resistance to the flow of fluids from fluid reservoir 176 and to thermal ablation device 162. Flush valve 188 further includes a plunger 224 which is lifted to draw fluids from fluid reservoir 176 through valve 220 and into flush valve 188 as shown in FIG. 18. To flush the fluid through the hollow body organ, plunger 224 is then depressed as illustrated in FIG. 19. In so doing, valve 220 closes and valve 222 opens to allow pressurized fluid (created by translation of plunger 224) into fluid line 178 where it will be flushed through the hollow body organ.

Although the foregoing invention has been described in detail for purposes of clarity of understanding, it will be obvious that certain modifications may be practiced within the scope of the appended claims.

What is claimed is:

1. A thermal ablation device for thermally treating a hollow body organ, the device comprising:
    an elongate member having a proximal end and a distal end;
    a heating apparatus operably attached to the elongate member near the distal end; and
    a fluid circulator operably attached to the elongate member, the fluid circulator including an elongate drive shaft having a proximal end which includes magnetic coupling, wherein the magnetic coupling is adapted to be coupled with a magnetic coupling of a drive unit to rotate the fluid circulator.

2. The device as in claim 1, wherein the fluid circulator further comprises an impeller located near the heating apparatus which is rotated upon rotation of the drive shaft.

3. The device as in claim 1, wherein the elongate member and the drive shaft are flexible.

4. The device as in claim 1, wherein the heating apparatus comprises a pair of spaced-apart electrodes.

5. The device as in claim 1, wherein the elongate member includes a heating chamber near the distal end, and wherein the heating apparatus is disposed within the heating chamber.

6. The device as in claim 1, wherein the magnetic coupling of the drive shaft is enclosed within the elongate member.

7. A thermal ablation system for thermally treating a hollow body organ, the system comprising:
    an elongate member having a proximal end and a distal end;
    a heating apparatus operably attached to the elongate member near the distal end;
    a fluid circulator operably attached to the elongate member, the fluid circulator including an elongate drive shaft having a proximal end and a magnetic coupling at the proximal end; and
    a drive unit comprising a rotatable magnetic coupling, wherein the drive shaft magnetic coupling may be coupled to the drive unit magnetic coupling to rotate the fluid circulator.

8. The system as in claim 7, further comprising at least one spacer to distance the magnetic couplings when magnetically coupled together.

9. The system as in claim 8, wherein the drive shaft is held within the elongate member, and wherein the spacer comprises the proximal end of the elongate member.

10. The system as in claim 9, wherein proximal end of the elongate member fluidically seals the elongate member from the drive unit.

11. The system as in claim 7, wherein the heating apparatus comprises a pair of spaced apart electrodes, and further comprising a radio frequency power supply coupled to the electrodes.

12. The system as in claim 11, wherein the elongate member includes an electrical interface to which the radio frequency power supply may be coupled.

13. The system as in claim 12, wherein the radio frequency power supply is included within a controller, and wherein the controller includes an electrical interface which is coupled to the electrical interface of the elongate member upon magnetic coupling of the couplings to supply radio frequency power to the electrodes.

14. The system as in claim 7, wherein the elongate member further includes an inflow lumen and an outflow lumen to deliver and remove a thermally conductive fluid to and from the hollow body organ.

15. The system as in claim 14, further comprising an open fluid reservoir in communication with the inflow lumen, said fluid reservoir holding a supply of the thermally conductive fluid.

16. A method for thermally ablating a hollow body organ, the method comprising:
    introducing a thermally conductive fluid and a heating apparatus having a fluid circulator into the hollow body organ so that the fluid circulator is within the hollow body organ;
    magnetically coupling the fluid circulator to a drive unit, and
    operating the drive unit to rotate the fluid circulator.

17. The method as in claim 16, further comprising fluidically sealing the fluid circulator from the drive unit.

18. The method as in claim 16, further comprising electrically isolating the fluid circulator from the drive unit.

19. The method as in claim 16, further comprising discarding the heating apparatus after use, and reusing the drive unit.

20. The method as in claim 16, further comprising heating the fluid without direct substantial heating of a heating element.

21. A thermal ablation system for thermally treating a hollow body organ which is filled with a fluid, the system comprising:
    a heating apparatus having a proximal end and a distal end, wherein the distal end is adapted to be received within the hollow body organ; and
    a flow sensor operably coupled to the heating apparatus to detect a change of volume of the fluid within the hollow body organ while the heating apparatus is within the hollow body organ.

22. The system as in claim 21, further comprising a controller, wherein the heating apparatus and the flow sensor are coupled to the controller, and wherein the controller ceases operation of the heating apparatus when the flow sensor senses a volume change that exceeds a threshold amount.

23. The system as in claim 21, further comprising a fluid reservoir which is adapted to be placed in communication with the hollow body organ to fill the hollow body organ with the fluid, and wherein the flow sensor comprises a drip chamber and means for detecting droplets passing through the drip chamber.

24. The system as in claim 23, wherein the fluid reservoir is open to the atmosphere.

25. The system as in claim 23, wherein the heating apparatus includes a fluid circulator to circulate the fluid within the hollow body organ.

26. A method for thermally treating a hollow body organ that is filled with a fluid, the method comprising:
    inserting a distal end of a heating apparatus into the hollow body organ;
    operating the heating apparatus to heat the fluid; and
    monitoring for a change in volume of the fluid within the hollow body organ while operating the heating apparatus.

27. The method as in claim 26, further comprising ceasing operation of the heating apparatus when a predetermined volume change of the fluid within the hollow body organ has been detected.

28. The method as in claim 27, placing a fluid reservoir in communication with the hollow body organ and detecting a flow of fluid from the reservoir to the hollow body organ to detect a change of volume of the fluid within the hollow body organ.

29. The method as in claim 28, further comprising placing a drip chamber below the reservoir and detecting droplets of fluid falling through the drip chamber to detect the flow of fluid.

30. The method as in claim 26, wherein the heating apparatus includes a fluid circulator and further comprising circulating the fluid with the fluid circulator while heating the fluid.

31. A thermal ablation system for thermally treating a hollow body organ, the system comprising:
   a heating apparatus which is adapted to be placed in the hollow body organ;
   a fluid reservoir and a fluid line which is attached to the fluid reservoir and is adapted to be placed in fluid communication with the hollow body organ;
   a first and a second one way valve disposed in the fluid line; and
   a plunger operably attached to the fluid line between the first and the second valves, wherein movement of the plunger in one direction draws fluid from the reservoir and through the first valve and movement of the plunger in another direction moves the fluid through the second valve and into the hollow body organ.

32. The system as in claim 31, wherein the fluid line is operably attached to a lumen in the heating apparatus, and wherein the fluid is delivered to the hollow body organ through the heating apparatus.

33. The system as in claim 31, wherein the fluid reservoir is open to the atmosphere.

34. A method for thermally treating the uterus, the method comprising:
   providing a heating apparatus comprising an elongate body having a proximal end, a distal end, at least one heating element and a fluid circulator near the distal end, wherein the elongate body is flexible at least near the distal end;
   introducing the distal end through the cervix until the distal end is within the uterus, with the elongate body bending within the cervix to generally center the distal end within the uterus; and
   operating the heating element when within the uterus.

35. The method as in claim 34, further comprising filling the uterus with a thermally conductive fluid and operating the fluid circulator to circulate the fluid.

36. The method as in claim 35, further comprising heating the fluid without substantial direct heating of the heating element.

37. A transcervical uterine access device comprising:
   a flexible elongate body having a proximal end and a distal end;
   a heating apparatus near the distal end; and
   a fluid circulator near the heating element, wherein the fluid circulator includes a flexible drive shaft extending through the flexible body.

38. A thermal ablation system for thermally treating a hollow body organ, the system comprising:
   a heating apparatus comprising an elongate body, at least one heating element and a fluid circulator;
   a fluid leak sensor which is adapted to detect leakage of fluid from the hollow body organ; and
   a controller, wherein the heating apparatus and the leak sensor are coupled to the controller to control operation of the heating apparatus and the leak sensor.

39. The system as in claim 38, wherein the leak sensor comprises a flow sensor for detecting a change of volume of the liquid within the hollow body organ.

40. The system as in claim 39, wherein the controller is configured to stop operation of the heating apparatus when the flow sensor senses a predetermined change of volume within the hollow body organ.

41. The system as in claim 38, wherein the heating apparatus further includes a drive unit to rotate the fluid circulator, and wherein the controller includes a power supply to supply power to the drive unit.

42. The system as in claim 38, wherein the heating element comprises a pair of electrodes, and wherein the controller includes a radio frequency power supply to supply power to the electrodes.

43. The system as in claim 42, wherein the heating apparatus further includes a temperature sensor to sense the temperature of the fluid within the hollow body organ, and wherein the controller includes a regulator to regulate the supply of radio frequency current supplied to the electrode based on the sensed temperatures.

44. The system as in claim 38, wherein the controller further includes a timer.

45. The system as in claim 38, wherein the controller further includes a drive unit monitor to monitor operating conditions of the drive unit.

46. A thermal ablation device for thermally treating a hollow body organ, the device comprising:
   an elongate member having a proximal end and a distal end;
   a first electrode operably attached to the elongate member near the distal end; and
   a fluid circulator operably attached to the elongate member, wherein at least a portion of the fluid circulator is conductive and serves as a second electrode.

47. The device as in claim 46, wherein the fluid circulator comprises a rotatable drive shaft and an impeller.

48. The device as in claim 47, wherein the drive shaft serves as the second electrode.

49. The device as in claim 47, wherein the impeller serves as the second electrode.

* * * * *